US012729218B2

(12) United States Patent
Jaffres et al.

(10) Patent No.: US 12,729,218 B2
(45) Date of Patent: Sep. 8, 2026

(54) GLYCOLIPIDS AND USE THEREOF AS SK3 ION CHANNEL MODULATORS

(71) Applicants: UNIVERSITÉ DE BRETAGNE OCCIDENTALE, Brest (FR); UNIVERSITÉ DE TOURS, Tours (FR); CENTRE NATIONAL DE LA RECHERCHE SCIENTIFIQUE, Paris (FR); INSTITUT NATIONAL DE LA SANTÉ ET DE LA RECHERCHE MÉDICALE, Paris (FR)

(72) Inventors: Paul Alain Jaffres, Bohars (FR); Hélène Couthon, Bohars (FR); Charlotte Sevrain, Douarnenez (FR); Alicia Bauduin, Brest (FR); Christophe Vandier, La Riche (FR); Aurélie Chantôme, Tours (FR); Delphine Fontaine, Tours (FR)

(73) Assignees: UNIVERSITÉ DE BRETAGNE OCCIDENTALE, Brest (FR); UNIVERSITÉ DE TOURS, Tours (FR); CENTRE NATIONAL DE LA RECHERCHE SCIENTIFIQUE, Paris (FR); INSTITUT NATIONAL DE LA SANTÉ ET DE LA RECHERCHE MÉDICALE, Paris (FR)

( * ) Notice: Subject to any disclaimer, the term of this patent is extended or adjusted under 35 U.S.C. 154(b) by 706 days.

(21) Appl. No.: 18/005,709

(22) PCT Filed: Jul. 16, 2021

(86) PCT No.: PCT/EP2021/069982

§ 371 (c)(1),
(2) Date: Jan. 17, 2023

(87) PCT Pub. No.: WO2022/013430

PCT Pub. Date: Jan. 20, 2022

(65) Prior Publication Data

US 2023/0287031 A1 Sep. 14, 2023

(30) Foreign Application Priority Data

Jul. 17, 2020 (EP) .................................... 20305829

(51) Int. Cl.

| | |
|---|---|
| ***C07H 15/02*** | (2006.01) |
| ***A61P 9/00*** | (2006.01) |
| ***C07H 15/04*** | (2006.01) |

(52) U.S. Cl.
CPC ................ *C07H 15/04* (2013.01); *A61P 9/00* (2018.01)

(58) Field of Classification Search
USPC ........................................................... 514/25
See application file for complete search history.

(56) References Cited

U.S. PATENT DOCUMENTS 9,161,944 B2 * 10/2015 Vandier .................. A61P 35/04

FOREIGN PATENT DOCUMENTS

WO 2011101408 A1 8/2011

OTHER PUBLICATIONS

Patani et al., Chemical Reviews, 1996, 96, pp. 3147-3176. (Year: 1996).*
International Search Report and Written Opinion issued on Oct. 8, 2021, in corresponding International Application No. PCT/EP2021/069982, 17 pages.
Govindarajan, "Amphiphilic glycoconjugates as potential anticancer chemotherapeutics", European Journal of Medicinal Chemistry, Oct. 2017, vol. 143, pp. 1208-1253.
Noseda et al., "Neoplastic Cell Inhibition with New Ether Lipid Analogs", Lipids, Nov. 1987, vol. 22, No. 11, pp. 878-883.
Arthur et al., "Glycosylated Antitumor Ether Lipids: Activity and Mechanism of Action", Anti-Cancer Agents in Medicinal Chemistry, Jan. 2014, vol. 14, No. 4, pp. 592-606.
Girault et al., "Targeting SKCa Channels in Cancer: Potential New Therapeutic Approaches", Current Medicinal Chemistry, 2012, vol. 19, No. 5, pp. 697-713.

* cited by examiner

*Primary Examiner* — Traviss C McIntosh, III
(74) *Attorney, Agent, or Firm* — Maier & Maier, PLLC

(57) ABSTRACT

New glycolipids derivatives of Formula (I)

(I)

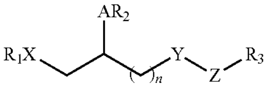

and their use in the treatment of diseases related with a deregulation of the expression and/or activity of SK3 ion channels. Also, pharmaceutical compositions including compounds of Formula (I) for use in the treatment of diseases related with a deregulation of the expression and/or activity of SK3 ion channels.

11 Claims, 5 Drawing Sheets

GLYCOLIPIDS AND USE THEREOF AS SK3 ION CHANNEL MODULATORS

FIELD OF INVENTION

The present invention relates to compounds useful as modulators of SK3 ion channel, in particular to new glycolipids compounds for use in the treatment of diseases related with a deregulation of the expression and/or activity of SK3 ion channels.

The present invention also relates to a process for manufacturing the compounds according to the invention.

BACKGROUND

Among the wide diversity of potassium channels, SKCa channels constitute a sub-class of channels that are activated and sensitive to cytosolic calcium concentration. This family of ion channels is composed of 3 channels isoforms (SK1, SK2, SK3 also identified as KCa2.1, KCa2.2, KCa2.3 with the genes KCNN1, KCNN2, KCNN3). These channels are implied in different physiological roles (e.g., regulation of neuronal excitability, sinoatrial node, implication in blood pressure regulation) and are also involved in pathological situations (e.g. neuronal disease, cancer, taxane-induced peripheral neuropathy (TIPN), cancer cell migration).

The conception of compounds that can modulate the activities of SKCa channels (activation or inhibition) was developed to assess the role of SKCa channels and for medical applications. Briefly, activation of SKCa channels was used concomitantly with N-methyl-D-aspartate receptor antagonists to produce antinociceptive effects. Other works have shown that the activation of SK2/SK3 channels improved the mobility of transgenic $SC_{A2}$ mice, and the activation of SK3 reduced inflammatory response activated by microglia. On the other hand, to mention few examples of the effect of the inhibition of SK3 channel, it is worth mentioning the possibility to reduce migration/invasion of microglia; SK3 blocker could reduce taxane-induced peripheral neuropathy. Of note, in some cancer cells the expression of SK3 channel is modified. For instance, in breast cancer cells (e.g. MDA-MB-435s) SK3 channel is expressed whereas in non-tumor cells this channel is not expressed. Interestingly, biopsies of cancer cells have shown that SK3 channels are also expressed in melanoma, breast and prostate cancer, and colon cancer biopsies. When SK3 channels is expressed in cancer cells it promotes at least cell migration.

As detailed in a recent review (Girault, A. et al. *Curr. Med. Chem.,* 2012, 19, 697-713) the first strategy to modulate the K+ currents triggered by SK3 channel consisted to use peptides (e.g. apamine), or heterocyclic compounds featuring cationic moieties (e.g. UCL1684, dequalinium). The inhibition can be also achieved by other classes of heterocyclic compounds that modified the sensitivity of cytosolic calcium concentration [Ca]cyt. (e.g. NS8593). On the other hand, other heterocyclic compounds were identified to activate SK3 channel (e.g. CyPPA, NS130018).

However, these compounds are known to be toxic and/or do not have the desired pharmacological properties to reach their target.

WO 2011/101408 discloses amphiphilic compounds to prevent cancer metastasis by inhibiting SK3 ion channel activity in tumor cells.

Deregulation of the expression and/or activity of SK3 ion channels is correlated with several pathological situations that inhibitors or activators of the SK3 channel could prevent or treat. There is thus a need to develop new compounds capable of modulate the expression and/or activity of SK3 ion channels while exhibiting a low toxicity.

The goal of this invention is to provide new amphiphilic compounds that are well tolerated and exhibit a low toxicity, providing therapeutic solutions to different pathologies in which SK3 ionic channels are involved.

Compounds according to the present invention features different hindrance and electronic demand depending on the type of sulfur function and its place. The position of the thioether function was also assessed jointly with the replacement of the methoxy group by an ethoxy group. As reported herein, these molecular modifications significantly modify the action of these new compounds on SK3 ion channels and allow to identify strong modulators of the expression and/or activity of SK3 ion channels.

SUMMARY

This invention thus relates to a compound of Formula (I):

(I)

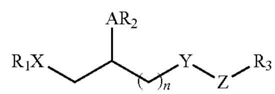

or a pharmaceutically acceptable salt or solvate thereof; wherein:

- $R_1$ is selected from a monosaccharide and a polysaccharide comprising from 2 to 6 monosaccharide units, preferably from 2 to 4;
- $R_2$ is selected from a $C_1$-$C_{10}$ alkyl, $C_2$-$C_{10}$ alkenyl and $C_1$-$C_{10}$ alkylaryl, preferably $R_2$ is a $C_1$-$C_6$ alkyl;
- $R_3$ is selected from an alkyl group, an alkenyl group and an alkylaryl group, said alkyl group, said alkenyl group or said alkylaryl group comprising from 10 to 25 carbon atoms, preferably from 15 to 20;
- A is selected from O, S, NH and $CH_2O$;
- X is selected from O, NH, S, —OP(O)(OH)O—, $CH_2$ and $CH_2$—$CH_2$;
- Y is selected from S, S(O), $S(O)_2$, $CH_2$ and CH═CH;
- Z is selected from S, S(O), $S(O)_2$, $CH_2$ and CH═CH; and
- n is an integer selected from 1 to 14, preferably from 1 to 5.

According to one embodiment, the invention relates to a compound having the Formula (II):

(II)

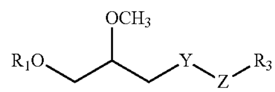

or a pharmaceutically acceptable salt or solvate thereof; wherein $R_1$, $R_3$, Y, Z are as defined for compounds of Formula (I).

According to one embodiment, the invention relates to a compound having the Formula (III):

(III)

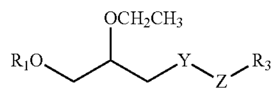

or a pharmaceutically acceptable salt or solvate thereof; wherein $R_1$, $R_3$, Y, Z are as defined for compounds of Formula (I).

According to one embodiment, $R_1$ is a disaccharide having its monosaccharide units linked together through a α-1,4, β-1,4, α-1,6 or β-1,6 linkage, preferably through a β-1,4 linkage.

According to one embodiment, $R_1$ is β-D-galactopyranosyl-(1→4)-D-glucopyranose.

According to one embodiment, $R_3$ is an alkyl group comprising from 15 to 18 carbon atoms.

According to one embodiment, Y is S and Z is $CH_2$.

According to one embodiment, Y is $CH_2$ and Z is S.

According to one embodiment, Y and Z are both a $CH_2$.

According to one embodiment, the compound of the invention is selected from:

001

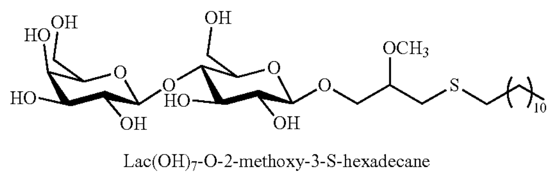

Lac(OH)7-O-2-methoxy-3-S-hexadecane

002

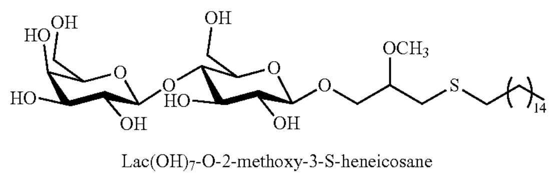

Lac(OH)7-O-2-methoxy-3-S-heneicosane

003

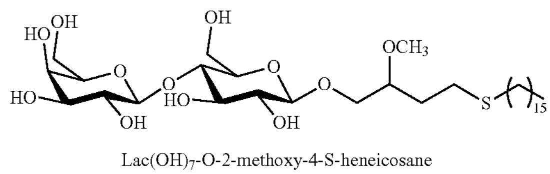

Lac(OH)7-O-2-methoxy-4-S-heneicosane

004

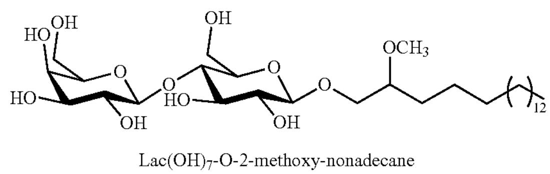

Lac(OH)7-O-2-methoxy-nonadecane

005

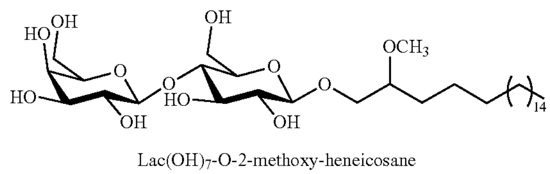

Lac(OH)7-O-2-methoxy-heneicosane

-continued

006

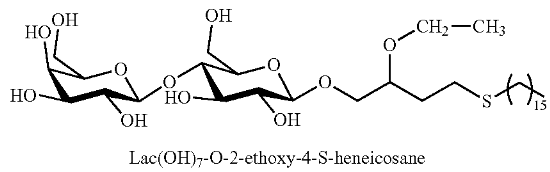

Lac(OH)7-O-2-ethoxy-4-S-heneicosane or pharmaceutically acceptable salts and solvates thereof.

This invention also relates to a compound according to the invention, as described hereinabove, for use as a medicament, preferably for use as a modulator of the expression and/or activity of SK3 ion channels.

According to one embodiment, the compound is for use in the treatment of a disease characterized by an excess of the expression and/or activity of SK3 ion channels, such as cancer cell migration and metastasis, chemotherapy-induced peripheral neuropathies, central nervous system diseases or auricular fibrillation.

According to one embodiment, the compound is for use in the treatment of a disease characterized by an insufficiency of the expression and/or activity of SK3 ion channels, such as infertility, preterm births, incontinence, erectile dysfunctions or systemic hypertension.

The invention also relates to a pharmaceutical composition comprising a compound according to the invention and at least one pharmaceutically acceptable carrier.

The invention also relates to a process for manufacturing a compound according to the invention comprising the following steps:

(a) glycosylation of compound of formula 1:

1

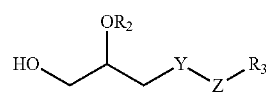

with a protected monosaccharide or polysaccharide activated at its anomeric position of formula 2:

2

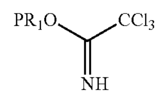

to produce compound 3:

3

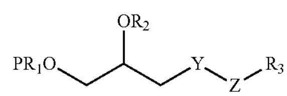

wherein Y, Z, $R_1$, $R_2$ and $R_3$ are as defined in claim 1, $R_1$ is a monosaccharide or polysaccharide; and (b) deprotection of the hydroxyl groups of the compound 3 obtained in step (a) to produce the compound having the general Formula (I), (I)

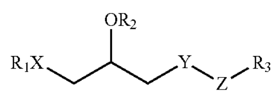

wherein Y, Z, $R_1$, $R_2$ and $R_3$ are as defined in claim 1, $R_1$ is a monosaccharide or polysaccharide and X is O.

The invention also relates to a process for manufacturing a compound according to the invention comprising the following steps:

(a) glycosylation of compound of formula 1:

1

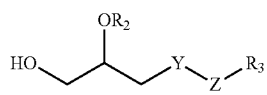

with a protected disaccharide activated at its anomeric position of formula 2:

2

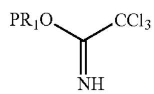

to produce compound 3:

3

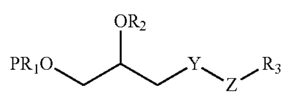

wherein Y, Z, $R_1$, $R_2$ and $R_3$ are as defined in claim 1, $R_1$ is a disaccharide; and (b) deprotection of the hydroxyl groups of the compound 3 obtained in step (a) to produce the compound having the general Formula (I), (I)

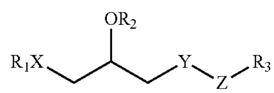

wherein Y, Z, $R_1$, $R_2$ and $R_3$ are as defined in claim 1, $R_1$ is a disaccharide and X is O.

BRIEF DESCRIPTION OF THE DRAWINGS

FIG. 1 (A,B,C) is a graph showing the recording of currents in condition control (vehicle application) and after exposition of compounds 002 (A), 003 (B) and 006 (C) at 10 μM. An addition of 100 nM apamin after exposition to 006 is used to inhibit residual SK3 currents.

DETAILED DESCRIPTION

Figure 1:
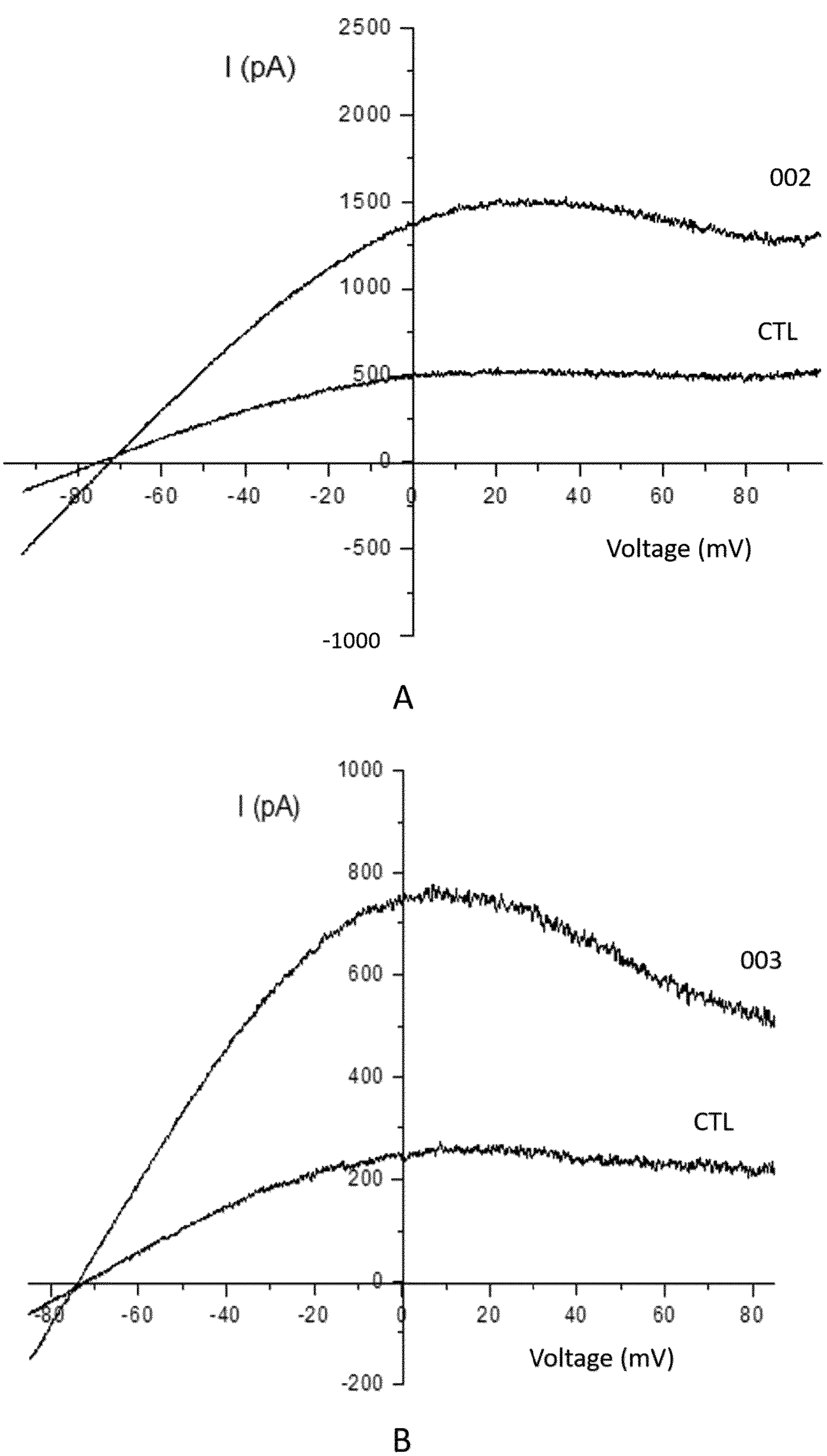
FIG. 1 (A, B, C) and FIG. 2 (A, B, C) show SK3 whole-cell currents recorded in HEK293T expressing SK3 channels before and after application of compounds 002, 003, and 006. Whole-cell currents were generated by ramp protocol from −90 to 90 mV in 500 ms from a constant holding potential of 0 mV with a pCa of 6.
Figure 1:
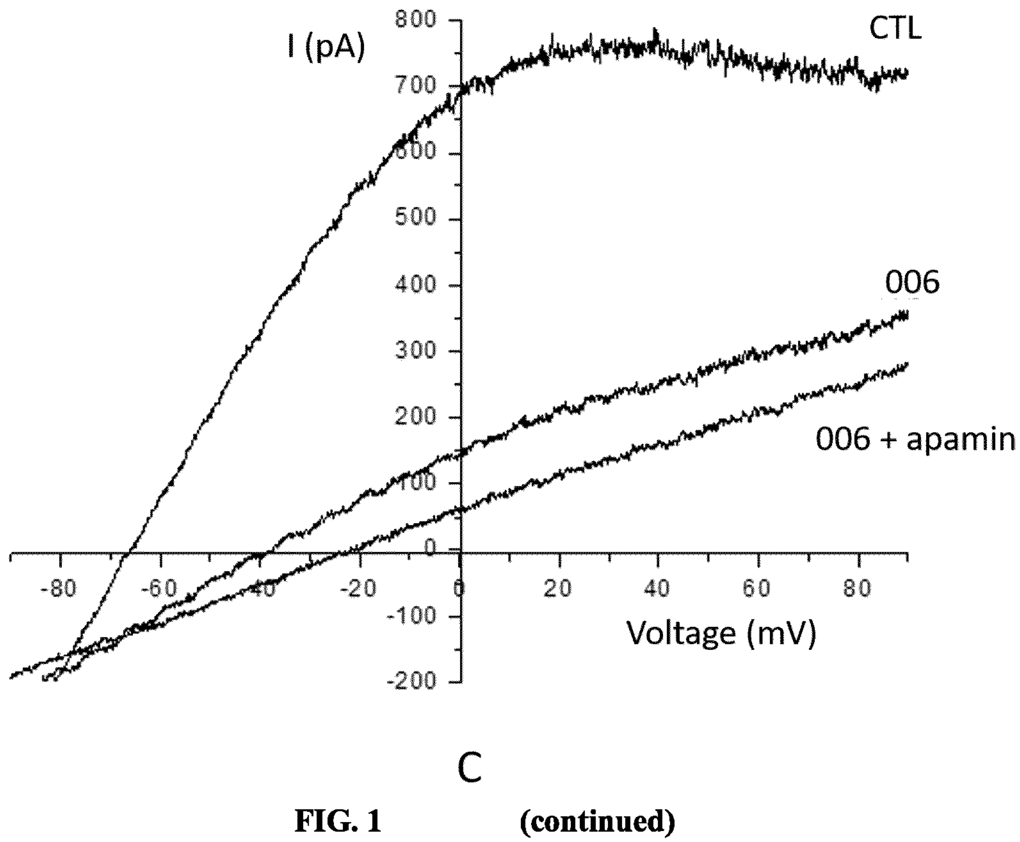

The definitions and explanations below are for the terms as used throughout the entire application, including both the specification and the claims.

When describing the compounds of the invention, the terms used are to be construed in accordance with the following definitions, unless indicated otherwise.

Unless indicated otherwise, the nomenclature of substituents that are not explicitly defined herein are arrived at by naming the adjacent functionality toward the point of attachment followed by the terminal portion of the functionality. For example, the substituent "arylalkyl" refers to the group -(aryl)-(alkyl).

In the present invention, the following terms have the following meanings:

The term "alkyl" by itself or as part of another substituent refers to a hydrocarbyl radical of formula $C_nH_{2n+1}$ wherein n is a number greater than or equal to 1. Generally, alkyl groups of this invention comprise, depending of the position of the alkyl group, from 1 to 20 carbon atoms. Alkyl groups may be linear or branched. Suitable alkyl groups include methyl, ethyl, n-propyl, i-propyl, n-butyl, i-butyl, s-butyl and t-butyl, pentyl and its isomers (e.g. n-pentyl, iso-pentyl), hexyl and its isomers (e.g. n-hexyl, iso-hexyl), heptyl and its isomers (e.g. n-heptyl, iso-heptyl), octyl and its isomers (e.g. n-octyl, iso-octyl), nonyl and its isomers (e.g. n-nonyl, iso-nonyl), decyl and its isomers (e.g. n-decyl, iso-decyl), undecyl and its isomers (e.g. n-undecyl, iso-undecyl), dodecyl and its isomers (e.g. n-dodecyl, iso-dodecyl), tridecyl and its isomers (e.g. n-tridecyl, iso-tridecyl), tetradecyl and its isomers (e.g. n-tetradecyl, iso-tetradecyl), pentadecyl and its isomers (e.g. n-pentadecyl, iso-pentadecyl), hexadecyl and its isomers (e.g. n-hexadecyl, iso-hexadecyl), heptadecyl and its isomers (e.g. n-heptadecyl, iso-heptadecyl), octadecyl and its isomers (e.g. n-octadecyl, iso-octadecyl), nonadecyl and its isomers (e.g. n-nonadecyl, iso-nonadecyl), eicosyl and its isomers (e.g. n-eicosyl, iso-eicosyl).

The term "alkenyl" as used herein refers to an unsaturated hydrocarbyl group, which may be linear or branched, comprising one or more carbon-carbon double bonds. Suitable alkenyl groups comprise between 2 and 20 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "aryl" as used herein refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, naphthalen-1- or -2-yl, 4-, 5-, 6 or 7-indenyl, 1- 2-, 3-, 4- or 5-acenaphthylenyl, 3-, 4- or 5-acenaphthenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

The term "halo" or "halogen" means fluoro, chloro, bromo, or iodo. Preferred halo groups are fluoro and chloro.

The term "haloalkyl" alone or as part of another group, refers to an alkyl radical having the meaning as defined above wherein one or more hydrogen atoms are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like. $C_x$-$C_y$-haloalkyl and $C_x$-$C_y$-alkyl are respectively haloalkyl and alkyl groups which comprise x to y carbon atoms. Preferred haloalkyl groups are difluoromethyl and trifluoromethyl.

Where at least one carbon atom in an aryl group is replaced with a heteroatom, the resultant ring is referred to herein as a heteroaryl ring.

The term "heteroalkyl" means an alkyl group as defined above in which one or more carbon atoms are replaced by a heteroatom selected from oxygen, nitrogen and sulfur atoms. In heteroalkyl groups, the heteroatoms are linked along the alkyl chain only to carbon atoms, i.e. each heteroatom is separated from any other heteroatom by at least one carbon atom. However, the nitrogen and sulphur heteroatoms may optionally be oxidized and the nitrogen heteroatoms may optionally be quaternized. A heteroalkyl is bonded to another group or molecule only through a carbon atom, i.e. the bonding atom is not selected from the heteroatoms included in the heteroalkyl group.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.

Where at least one carbon atom in a cycloalkyl group is replaced with a heteroatom, the resultant ring is referred to herein as "heterocycloalkyl" or "heterocyclyl".

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulf oxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

"Modulator" refers to a natural or synthetic compound that has a biological effect to activate or inhibit the expression of a gene and/or a protein, or that has a biological effect to activate or inhibit the biological activity of a protein. Consequently, "an SK3 ion channels modulator" refers to a synthetic compound that has a biological effect to activate or inhibit the expression of SK3 ion channels, or that has a biological effect to activate or inhibit the biological activity of SK3 ion channels.

"Monosaccharide" refers to polyhydroxy aldehydes or polyhydroxy ketones, comprising at least three carbon atoms. Non-limitative examples of monosaccharides are trioses (glyceraldehyde, dihydroxyacetone); tetroses (erythrose, threose, erythrulose); pentoses (desoxyribose, ribose, arabinose, xylose, lyxose, ribulose, xylulose); hexoses (allose, altrose, galactose, glucose, gulose, idose, mannose, talose); ketohexoses (psicose, fructose, sorbose, tagatose); desoxy-hexoses (fucose, rhamnose); heptoses (sedoheptulose, mannoheptulose); nonoses (neuraminic acid or sialic acid). The term also includes amino-containing monosaccharide. Non limitative example of amino-containing monosaccharides are L-vancosamine, 3-desmethyl-vancosamine, 3-epi-dausamine, epi-vancosamine, acosamine, actinosamine, daunosamine, 3-epi-daunosamine, ritosamine or N-methyl-D-glucamine. The term also includes cyclic polyols and phosphorylated monosaccharide. All references to "monosaccharide" include references to the linear or the cyclic form, pyranosyl and furanosyl.

"Polysaccharide" refers to a polymeric carbohydrate molecule composed of long chains of monosaccharide units bound together by glycosidic linkages; which may be linear or branched. Polysaccharides may for example be "homopolysaccharides", i.e. consisting of a plurality of identical monosaccharide units. Alternatively, polysaccharides may for example be "heteropolysaccharides", i.e. consisting of a plurality of at least two distinct monosaccharide units. Generally, polysaccharides comprise from 2 to 6 monosaccharide units, preferably from 2 to 4, more preferably two monosaccharide units ("disaccharide"). The monosaccharide units may for example be linked together through an $\alpha$-1,1 linkage, a $\beta$-1,1 linkage, an $\alpha$-1,2 linkage a $\beta$-1,2 linkage, an $\alpha$-1,3 linkage, a $\beta$-1,3 linkage, an $\alpha$-1,4 linkage, a $\beta$-1,4 linkage, $\alpha$-1,5 linkage, a $\beta$-1,5 linkage, an $\alpha$-1,6 linkage, a $\beta$-1,6 linkage or any combination thereof.

The term "solvate" is used herein to describe a molecular complex comprising a compound of the invention and contains stoichiometric or sub-stoichiometric amounts of one or more pharmaceutically acceptable solvent molecule such as ethanol. The term "hydrate" refers to a solvate when said solvent is water.

The term "human" refers to a subject of both genders and at any stage of development (i.e., neonate, infant, juvenile, adolescent, adult).

The term "patient" refers to a warm-blooded animal, more preferably a human, who/which is awaiting the receipt of, or is receiving medical care or is/will be the object of a medical procedure.

The term "active ingredient" refers to a molecule or a substance whose administration to a subject slows down or stops the progression, aggravation, or deterioration of one or more symptoms of a disease, or condition; alleviates the symptoms of a disease or condition; cures a disease or condition. According to one embodiment, the therapeutic ingredient is a small molecule, either natural or synthetic. According to another embodiment, the therapeutic ingredient is a biological molecule such as for example an oligonucleotide, a siRNA, a miRNA, a DNA fragment, an aptamer, an antibody and the like.

By "pharmaceutically acceptable" is meant that the ingredients of a pharmaceutical composition are compatible with each other and not deleterious to the patient thereof.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions and liposomes.

The term "pharmaceutically acceptable carrier" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, e.g., FDA Office or EMA.

The term "pharmaceutically acceptable excipient" refers to an inert vehicle or carrier used as a solvent or diluent in which the pharmaceutically active agent is formulated and/or administered, and which does not produce an adverse, allergic or other reaction when administered to an animal, preferably a human being. This includes all solvents, dispersion media, coatings, antibacterial and antifungal agents, isotonic agents, absorption retardants and other similar ingredients. For human administration, the preparations must meet standards of sterility, general safety and purity as required by regulatory agencies such as the FDA or EMA. For the purposes of the invention, "pharmaceutically acceptable excipient" includes all pharmaceutically acceptable excipients as well as all pharmaceutically acceptable carriers, diluents, and/or adjuvants.

The term "administration", or a variant thereof (e.g., "administering"), means providing the active agent or active ingredient (e.g., glycolipids of the invention), alone or as part of a pharmaceutically acceptable composition, to the patient in whom/which the condition, symptom, or disease is to be treated or prevented.

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g., glycolipids of the invention) that is sufficient to achieve the desired therapeutic or prophylactic effect in the patient to which/whom it is administered.

"Pharmaceutically acceptable salts" include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, 2-(diethylamino)ethanol, diolamine, ethanolamine, glycine, 4-(2-hydroxyethyl)-morpholine, lysine, magnesium, meglumine, morpholine, olamine, potassium, sodium, tromethamine and zinc salts.

Hemisalts of acids and bases may also be formed, for example, hemisulphate and hemicalcium salts.

Pharmaceutically acceptable salts of compounds of Formula (I) may be prepared by one or more of these methods:

(i) by reacting the compound of Formula (I) with the desired acid;

(ii) by reacting the compound of Formula (I) with the desired base;

(iii) by removing an acid- or base-labile protecting group from a suitable precursor of the compound of Formula (I) or by ring-opening a suitable cyclic precursor, e.g., a lactone or lactam, using the desired acid; and/or (iv) by converting one salt of the compound of Formula (I) to another by reaction with an appropriate acid or by means of a suitable ion exchange column.

All these reactions are typically carried out in solution. The salt may precipitate from solution and be collected by filtration or may be recovered by evaporation of the solvent. The degree of ionization in the salt may vary from completely ionized to almost non-ionized.

Although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

Compound

This invention relates to a compound of Formula (I):

(I)

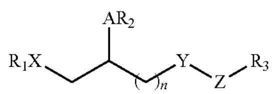

or a pharmaceutically acceptable salt or solvate thereof; wherein:

$R_1$ is selected from cyclic polyol, phosphorylated polyhydroxy, monosaccharide and a polysaccharide comprising from 2 to 6 monosaccharide units;

$R_2$ is selected from a $C_1$-$C_{10}$ alkyl, $C_2$-$C_{10}$ alkenyl, $C_1$-$C_{10}$ alkylaryl;

$R_3$ is selected from an alkyl group, an alkenyl group, and an alkylaryl group, said alkyl group, said alkenyl group or said alkylaryl comprising from 10 to 25 carbons atoms, preferably from 15 to 20;

A is selected from O, S, NH and $CH_2O$;

X is selected from O, NH, S, —OP(O)(OH)O—, $CH_2$ and $CH_2$—$CH_2$;

Y is selected from S, S(O), $S(O)_2$, $CH_2$ and CH═CH;

Z is selected from S, S(O), $S(O)_2$, $CH_2$ and CH═CH and n is an integer selected from 1 to 14.

According to one embodiment, $R_1$ is a monosaccharide selected from the group comprising pentosyl, hexosyl or ketohexosyl. In one embodiment, $R_1$ is a pentosyl group. In a preferred embodiment, $R_1$ is an hexosyl group.

According to one embodiment, $R_1$ is a polysaccharide comprising from 2 to 6 monosaccharide units. In a preferred embodiment, $R_1$ is a polysaccharide comprising from 2 to 4 monosaccharide units. In one embodiment, the monosaccharide units are linked together through a α-1,1 linkage. In one embodiment, the monosaccharide units are linked together through a β-1,1 linkage. In one embodiment, the monosaccharide units are linked together through an α-1,2 linkage. In one embodiment, the monosaccharide units are linked together through a β-1,2 linkage. In one embodiment, the monosaccharide units are linked together through an α-1,3 linkage. In one embodiment, the monosaccharide units are linked together through a β-1,3 linkage. In one embodiment, the monosaccharide units are linked together through an α-1,4 linkage. In one embodiment, the monosaccharide units are linked together through a β-1,4 linkage. In one embodiment, the monosaccharide units are linked together through an α-1,5 linkage. In one embodiment, the monosaccharide units are linked together through a β-1,5 linkage. In one embodiment, the monosaccharide units are linked together through an α-1,6 linkage. In one embodiment, the monosaccharide units are linked together through a (β-1,6 linkage.

In these embodiments, the monosaccharide units are selected from pentosyl, hexosyl and ketohexosyl, preferably from hexosyl group.

According to one embodiment, the pentosyl group has the formula (A):

(A)

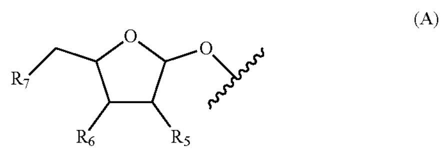

wherein $R_5$, $R_6$ and $R_7$ are independently selected from hydroxyl, methoxy, acetoxy, acetyloxy, amino and acetylamino.

In one embodiment, $R_5$, $R_6$ and $R_7$ are independently selected from hydroxyl and acetyloxy.

In one embodiment, $R_5$, $R_6$ and $R_7$ are identical and represent each an acetyloxy.

In a preferred embodiment, $R_5$, $R_6$ and $R_7$ are identical and represent each a hydroxyl.

According to one embodiment, the pentosyl group is selected from D or L-ribosyl, D or L-xylosyl, D or L-arabinosyl and D or L-lyxosyl.

According to one embodiment, the hexosyl group has the formula (B):

(B)

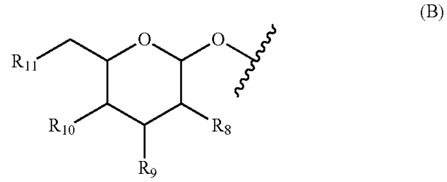

wherein $R_8$, $R_9$, $R_{10}$ and $R_{11}$ are independently selected from hydroxyl, methoxy, acetoxy, acetyloxy, amino and acetylamino.

In one embodiment, $R_8$, $R_9$, $R_{10}$ and $R_{11}$ are independently selected from hydroxyl and acetyloxy.

In one embodiment, $R_8$, $R_9$, $R_{10}$ and $R_{11}$ are identical and represent each an acetyloxy. In a preferred embodiment, $R_8$, $R_9$, $R_{10}$ and Ru are identical and represent each a hydroxyl.

According to one embodiment, the hexosyl group is selected from D or L-glucosyl, D or L-galactosyl, D or L-mannosyl, D or L-allosyl, D or L-altrosyl, D or L-gulosyl, D or L-idosyl and D or L-talosyl. In on embodiment, the hexosyl group is selected from D-glucosyl and D-galactosyl.

One skilled in the art easily understands that, for monosaccharides of formula (A) and (B) and, by analogy and whenever suitable, for any other $R_1$, the oxygen atom that is represented just before the linkage to the rest of the molecule corresponds to X atom of formulae (I), (II) and (III).

According to one embodiment, $R_1$ is a homopolysaccharide. In one embodiment, $R_1$ is a heteropolysaccharide.

According to a preferred embodiment, $R_1$ is disaccharide.

According to one embodiment, $R_1$ is a disaccharide selected from β-D-galactopyranosyl-(1→4)-D-glucopyranose, α-D-glucopyranosyl-(1→4)-D-glucopyranose, α-D-galactopyranosyl-(1→6)-D-glucospyranose, β-D-glucopyranosyl-(1→4)-D-glucopyranose, 3-D-glucopyranosyl-(1→6)-D-glucopyranose, α-D-glucopyranosyl-(1→6)-D-glucopyranose, 3-D-glucopyranosyl-(1→2)-D-glucopyranose, α-D-glucopyranosyl-(1→6)-D-galactopyranose and β-D-glucopyranosyl-(1→3)-D-glucopyranose.

In a preferred embodiment, $R_1$ is selected from β-D-galactopyranosyl-(1→4)-D-glucopyranose, α-D-glucopyranosyl-(1→4)-D-glucopyranose and α-D-alactopyranosyl-(1→6)-D-glucospyranose.

In a more preferred embodiment, $R_1$ is β-D-galactopyranosyl-(1→4)-D-glucopyranose.

According to one embodiment, $R_2$ is a $C_1$-$C_{10}$ alkyl. In one embodiment, $R_2$ is a $C_1$-$C_6$ alkyl. In one embodiment, $R_2$ is a $C_1$-$C_3$ alkyl. In one embodiment, $R_2$ is a $C_1$-$C_2$ alkyl. In a preferred embodiment, $R_2$ is a methyl. In another preferred embodiment, $R_2$ is an ethyl.

According to one embodiment, $R_3$ is selected from a $C_{15}$-$C_{20}$ alkyl group and a $C_{15}$-$C_{20}$ alkenyl group. In one embodiment, $R_3$ is a $C_{15}$-$C_{20}$ alkyl group. In a preferred embodiment, $R_3$ is a $C_{15}$-$C_{18}$ alkyl group. In a more preferred embodiment, $R_3$ is an alkyl group comprising 15 or 16 carbon atoms.

According to a preferred embodiment, A is an oxygen.

According to a preferred embodiment, X is an oxygen.

According to one embodiment, Y is selected from S or $CH_2$. In a preferred embodiment, Y is a sulfur atom. In another preferred embodiment, Y is a $CH_2$.

According to one embodiment, Z is selected from S or $CH_2$. In a preferred embodiment, Z is a sulfur atom. In another preferred embodiment, Z is a $CH_2$.

According to a preferred embodiment, Y and Z are different. In a preferred embodiment, when Y is a sulfur atom, Z is a $CH_2$. In another preferred embodiment, when Y is a $CH_2$, Z is a sulfur atom.

According to another preferred embodiment, Y and Z are identical and represent each a $CH_2$.

According to one embodiment, n is an integer selected from 1 to 5. In one embodiment, n is an integer selected from 1 to 3. In one embodiment, n is 1 or 2. In a preferred embodiment, n is 1.

According to an embodiment, preferred compounds of general Formula (I) are those wherein:

$R_1$ is a disaccharide selected from β-D-galactopyranosyl-(1→4)-D-glucopyranose, α-D-glucopyranosyl-(1→4)-D-glucopyranose or α-D-alactopyranosyl-(1→6)-D-glucospyranose;

$R_2$ is an alkyl group comprising 1 or 2 carbon atoms;

$R_3$ is an alkyl group comprising 15 to 18 carbon atoms;

A is an oxygen;

X is an oxygen;

Y is selected from S or $CH_2$;

Z is selected from S or $CH_2$; and n is 1.

According to a preferred embodiment, the invention relates to compounds of general Formula (II),

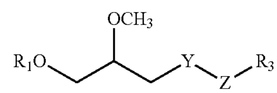

(II)

or a pharmaceutically acceptable salt or solvate thereof, corresponding to the compounds of Formula (I) wherein X is an oxygen and $R_2$ is a methyl and wherein $R_1$, $R_3$, Y, Z are as defined herein above for compounds of Formula (I). According to an embodiment, preferred compounds of general Formula (II) are those of Formula (II-1),

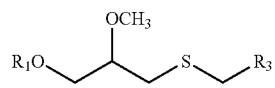

(II-1)

or a pharmaceutically acceptable salt or solvate thereof, wherein Y is a sulfur and Z is a $CH_2$ and wherein $R_1$ and $R_3$ are as defined herein above for compounds of Formula (I).

According to an embodiment, preferred compounds of general Formula (II) are those of Formula (II-2),

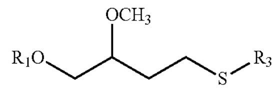

(II-2)

or a pharmaceutically acceptable salt or solvate thereof, wherein Y is a $CH_2$ and Z is a sulfur and wherein $R_1$ and $R_3$ are as defined herein above for compounds of Formula (I).

According to an embodiment, preferred compounds of general Formula (II) are those of Formula (II-3),

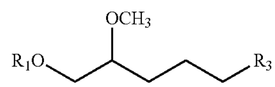

(II-3)

or a pharmaceutically acceptable salt or solvate thereof, wherein Y and Z are a $CH_2$ and wherein $R_1$ and $R_3$ are as defined herein above for compounds of Formula (I).

According to another preferred embodiment, the invention relates to compounds of general Formula (III), (III)

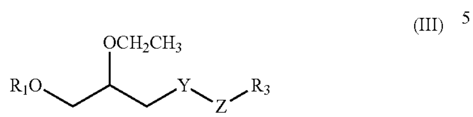

or a pharmaceutically acceptable salt or solvate thereof, corresponding to the compounds of Formula (I) wherein X is an oxygen and $R_2$ is an ethyl and wherein $R_1$, $R_3$, Y, Z are as defined herein above for compounds of Formula (I).

According to an embodiment, preferred compounds of general Formula (III) are those of Formula (III-1), (III-1)

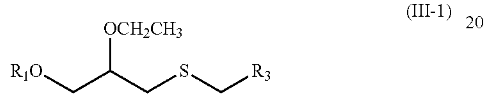

or a pharmaceutically acceptable salt or solvate thereof, wherein Y is a sulfur and Z is a $CH_2$ and wherein $R_1$ and $R_3$ are as defined herein above for compounds of Formula (I).

According to an embodiment, preferred compounds of general Formula (III) are those of Formula (III-2), (III-2)

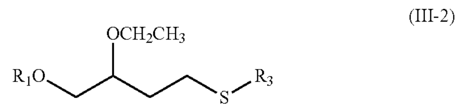

or a pharmaceutically acceptable salt or solvate thereof, wherein Y is a $CH_2$ and Z is a sulfur and wherein $R_1$ and $R_3$ are as defined herein above for compounds of Formula (I).

According to an embodiment, preferred compounds of general Formula (III) are those of Formula (III-3), (III-3)

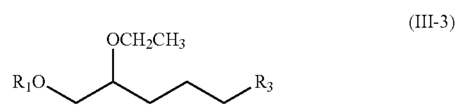

or a pharmaceutically acceptable salt or solvate thereof, wherein Y and Z are a $CH_2$ and wherein $R_1$ and $R_3$ are as defined herein above for compounds of Formula (I).

According to one embodiment, the compound according to the invention is selected from:

TABLE 1

| | | |
|---|---|---|
| 001 | 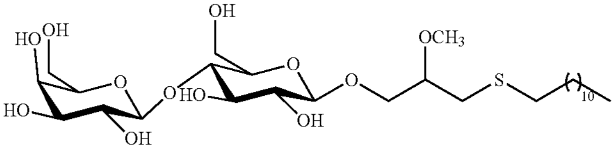 | $Lac(OH)_7$-O-2-methoxy-3-S-hexadecane |
| 002 | 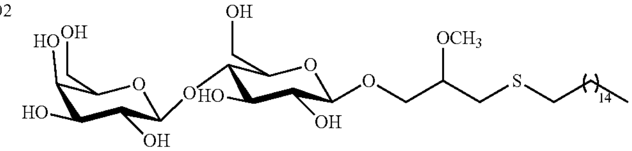 | $Lac(OH)_7$-O-2-methoxy-3-S-heneicosane |
| 003 | 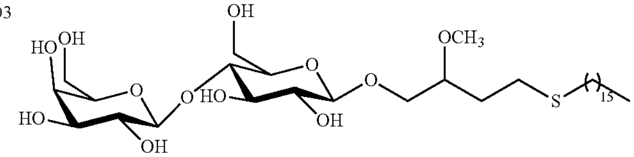 | $Lac(OH)_7$-O-2-methoxy-4-S-heneicosane |
| 004 | 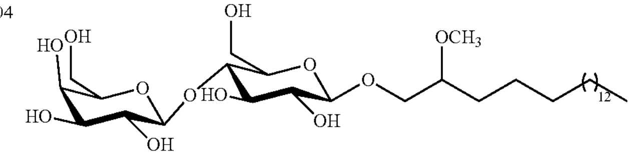 | $Lac(OH)_7$-O-2-methoxy-nonadecane |
| 005 | 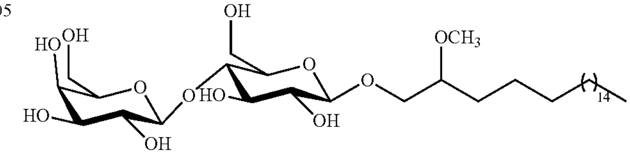 | $Lac(OH)_7$-O-2-methoxy-heneicosane |

TABLE 1-continued

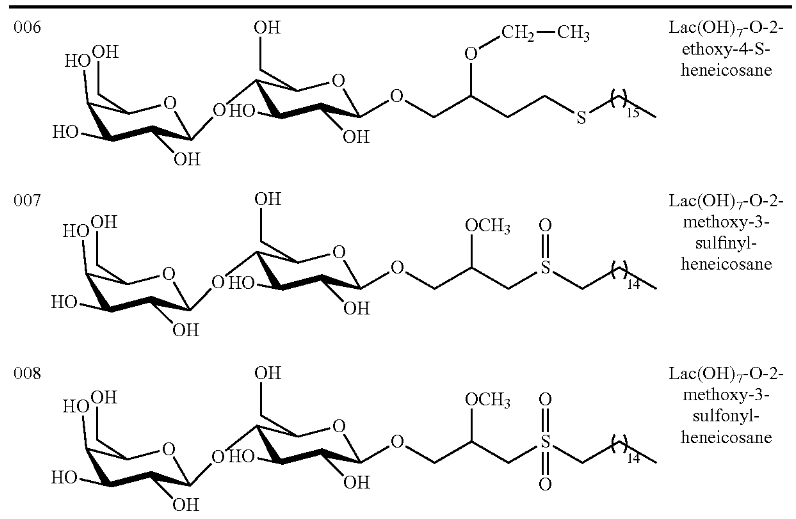

006 Lac(OH)$_7$-O-2-ethoxy-4-S-heneicosane

007 Lac(OH)$_7$-O-2-methoxy-3-sulfinyl-heneicosane

008 Lac(OH)$_7$-O-2-methoxy-3-sulfonyl-heneicosane and pharmaceutically acceptable salts and solvates thereof.

According to one embodiment, preferred compound of the invention are compounds 002-006.

The compounds of Formula (I)-(III) and subformulae thereof contain at least one asymmetric centre(s) and thus may exist as different stereoisomeric forms. Accordingly, all references to compounds of Formula (I)-(III) include references to all possible stereoisomers and includes not only the racemic compounds but the individual enantiomers and their non-racemic mixtures as well. When a compound is desired as a single enantiomer, such single enantiomer may be obtained by stereospecific synthesis, by resolution of the final product or any convenient intermediate, or by chiral chromatographic methods as each are known in the art. Resolution of the final product, an intermediate, or a starting material may be carried out by any suitable method known in the art.

Pharmaceutical Composition

This invention also relates to a pharmaceutical composition comprising a compound according to the invention, as described hereinabove, and at least one pharmaceutically acceptable carrier.

According to a second embodiment, the pharmaceutical composition further comprises at least another active ingredient. In one embodiment, the other active ingredient is selected from taxanes, such as paclitaxel, docetaxel or cabazitaxel.

Process

According to another aspect, the invention relates to a method for the preparation of the compounds of Formula (I)-(III), which means Formula (I), (II) or (III), as described above.

In particular, the compounds of Formula (I)-(III) disclosed herein may be prepared as described below from substrates 1-8. It shall be understood by a person skilled in the art that these schemes are in no way limiting and that variations may be made without departing from the spirit and scope of this invention.

According to one embodiment, the compounds having the general Formula (I)-(III), wherein Y is a S and Z is a $CH_2$, are synthesized according to the pathway described in Scheme 1, starting from the thioether analogues 1 as precursors.

The method involves in a first step the glycosylation of compound 1 with a protected monosaccharide or polysaccharide, preferably a protected disaccharide, 2 activated at its anomeric position with a trichloroacetimidate moiety to produce compound 3, wherein $R_1$, $R_2$ and $R_3$ are as defined herein above for compounds of Formula (I).

According to one embodiment, the glycosylation reaction is performed in presence of a Lewis acid. Non-limiting examples of Lewis acids include TMSOTf, $BF_3 \cdot OEt_2$, $TiCl_4$ and $FeCl_3$.

According to one embodiment, any hydroxyl group of the activated monosaccharide or polysaccharide is protected with an appropriate protecting group known to the skilled person in the art. According to one embodiment, the appropriate protecting group is an acetyl group.

The second step involves the deprotection of the hydroxyl groups to produce compounds having the general Formula (I)-(III), wherein Y is a S and Z is a $CH_2$ and wherein $R_1$, $R_2$ and $R_3$ are as defined herein above for compounds of Formula (I).

The choice and the exchange of the protective groups are within the competence of the skilled person in the art. Protective groups can be removed by methods well known to the skilled person in the art, for example, with an acid (e.g., a mineral or organic acid), a base, or a fluoride source.

For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Scheme 1 Synthesis of compounds of Formula (I)-(III), wherein Y is a S and Z is a $CH_2$.

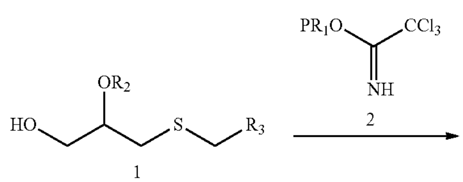

1

2

-continued

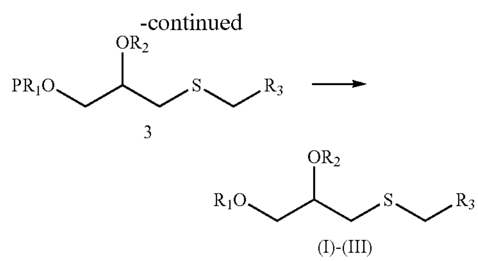

3

(I)-(III)

According to one embodiment, the compounds having the general Formula (I)-(III), wherein Y is a $CH_2$ and Z is a S, are synthesized according to the pathway described in Scheme 2.

The method involves in a first step the synthesis of the vinyl alcohol 4 by a regioselective opening of the vinyl epoxide in acidic media by adapting a reported procedure (Williams, D. B. G. et al. *Org. Biomol. Chem.* 2005, 3, 3269-3272).

In a second step, compound 4 is engaged in a photo-click thiol-ene reaction with the thiol 5 to produce compound 6 wherein $R_2$ and $R_3$ are as defined herein above for compounds of Formula (I). For this reaction, the conditions were inspired from a procedure previously optimized to prepare other types of amphiphilic compounds (Wimmer, A. et al. *J. Org. Chem.* 2018, 14, 54-83).

The intermediate compound 6 is then engaged in a glycosylation reaction with the protected disaccharide 2 activated at its anomeric position, in presence of a Lewis acid to produce compound 7 wherein $R_1$, $R_2$ and $R_3$ are as defined herein above for compounds of Formula (I).

The last step involves the deprotection of hydroxyl groups to produce compounds having the general Formula (I)-(III), wherein Y is a $CH_2$ and Z is a S and wherein $R_1$, $R_2$ and $R_3$ are as defined herein above for compounds of Formula (I).

Scheme 2 Synthesis of compounds of Formula (I)-(III), wherein Y is a $CH_2$ and Z is a S.

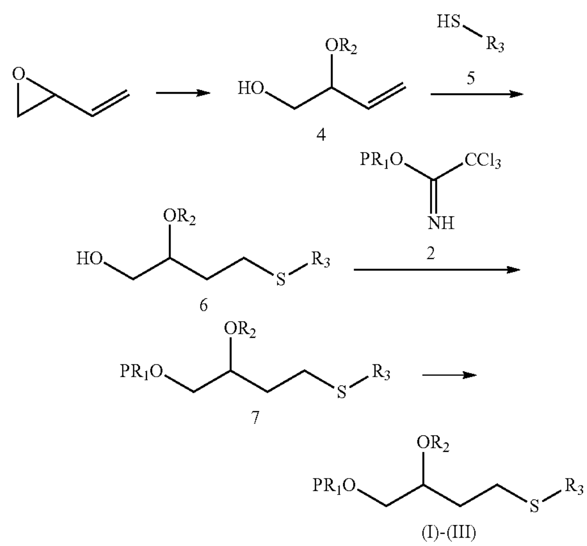

4, 5, 6, 2, 7, (I)-(III)

According to one embodiment, the compounds having the general Formula (I)-(III), wherein Y and Z are a $CH_2$, are synthesized according to the pathway described in Scheme 3.

The method involves in a first step the synthesis of the mono protected diol 9 by a regioselective opening of the epoxide 8.

In a second step, compound 9 is engaged in an alkylation reaction to produce compound 10 wherein $R_2$ and $R_3$ are as defined herein above for compounds of Formula (I).

The protected hydroxy group of compound 10 is then deprotected to produce compound 11.

The intermediate compound 11 is then engaged in a glycosylation reaction with the protected disaccharide 2 activated at its anomeric position, in presence of a Lewis acid to produce compound 12 wherein $R_1$, $R_2$ and $R_3$ are as defined herein above for compounds of Formula (I).

The last step involves the deprotection of hydroxyl groups to produce compounds having the general Formula (I)-(III), wherein Y is a $CH_2$ and Z is a $CH_2$, and wherein $R_1$, $R_2$ and $R_3$ are as defined herein above for compounds of Formula (I).

Scheme 3 Synthesis of compounds of Formula (I)-(III), wherein Y and Z are a $CH_2$.

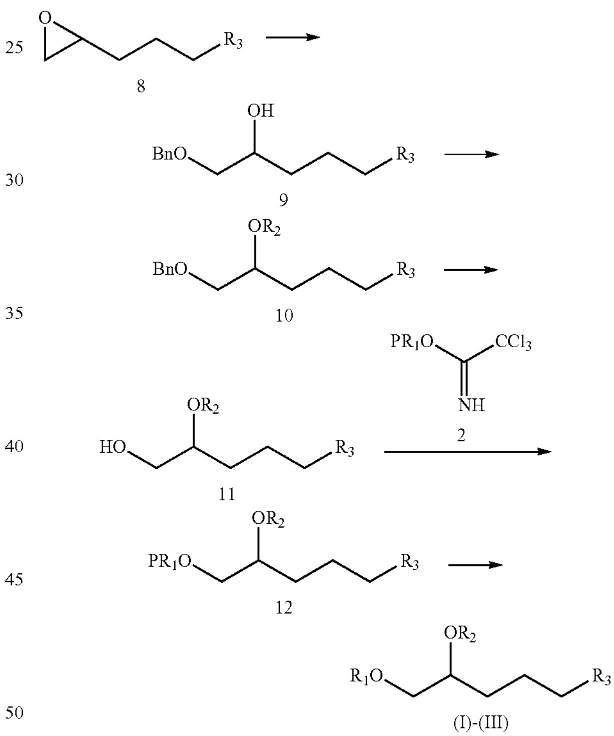

8, 9, 10, 2, 11, 12, (I)-(III)

According to one embodiment, the compounds having the general Formula (I)-(III), wherein Y is a S(O) or $S(O)_2$ and Z is a $CH_2$, are synthesized according to the pathway described in Scheme 4, starting from the thioether analogues 1 as precursor.

The method involves in a first step the oxidation of compound 1 with mCPBA to produce, depending of the number of equivalents of mCPBA, compounds 13a or 13b wherein Y is S(O) or $S(O)_2$ and wherein $R_1$, $R_2$ and $R_3$ are as defined herein above for compounds of Formula (I).

The second and third steps involve respectively the glycosylation of compounds 13a and 13b, as described herein above, to produce compounds 14a and 14b, followed by the deprotection of hydroxyl groups, as described herein above, to produce compounds having the general Formula (I)-(III), wherein Y is S(O) or $S(O)_2$ and wherein $R_1$, $R_2$ and $R_3$ are as defined herein above for compounds of formula (I).

Scheme 4 Synthesis of compounds of Formula (I)-(III), wherein Y is S(O) or $S(O)_2$ and Z is a $CH_2$.

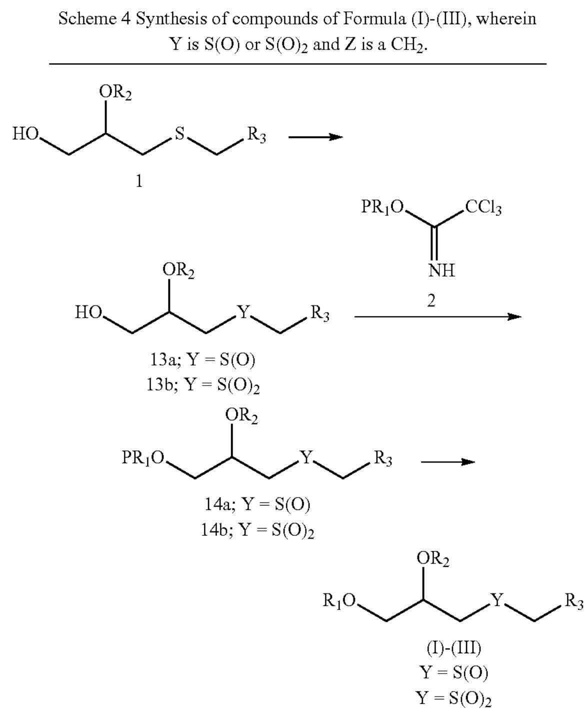

1

2

13a; Y = S(O)
13b; Y = $S(O)_2$

14a; Y = S(O)
14b; Y = $S(O)_2$ (I)-(III)
Y = S(O)
Y = $S(O)_2$

In general, the synthesis pathways for any individual compound of Formula (I)-(III) will depend on the specific substituents of each molecule and upon the ready availability of intermediates necessary; again, such factors being appreciated by those of ordinary skill in the art.

Medical Use and Methods of Treatment

This invention relates to a compound according to the invention, as described hereinabove, for use as a medicament.

Interestingly and without being linked by any theory, it was found that the compound of the invention may act on SK3 ion channels by generating a modification of the bio-physical properties of the membrane and/or by a direct interaction with the SK3 protein. Its action could be view as an illustration of the concept of membrane lipid therapy.

Without willing to be linked by any theory, the long alkyl chain of the compound of the invention may acts as a membrane anchor, whereas the glycerol moiety in combination with the saccharide part interact with the polar groups of the constituents of the plasma membranes (e.g. phospholipid, cholesterol).

According to one embodiment, the invention also relates to a compound according to the invention, as described hereinabove, for use as modulator of the expression and/or activity of SK3 ion channels.

According to one embodiment, the invention relates to a compound according to the invention, as described hereinabove, for use as inhibitor of the expression and/or activity of SK3 ion channels.

According to one embodiment, the invention relates to a compound according to the invention, as described hereinabove, for use as activator of the expression and/or activity of SK3 ion channels.

According to one embodiment, the invention relates to a compound according to the invention, as described hereinabove, for use in the treatment of a disease related with a deregulation of the expression and/or activity of SK3 ion channels.

According to one embodiment, the invention relates to a compound according to the invention, as described hereinabove, for use in the treatment of a disease characterized by an excess of the expression and/or activity of SK3 ion channels. Non-limiting examples of such diseases are:

- cancer cell migration and metastasis. The expression of SK3 in cancerous cells leads to migration properties of these cells and consequently participates in the complex mechanism of metastasis formation;
- chemotherapy-induced peripheral neuropathies. SK3 channels and in particular the short forms are involved in taxane-induced secondary neuropathies;
- central nervous system diseases. With age an increase in the expression of SK3 channels was observed in neuronal cells of the hippocampus leading to a reduction in long-term potentiation. Inhibitors of the SK3 channel could promote potentiation; and
- auricular fibrillation. The SK3 channel regulates the duration of the auricular action potential via its effect on repolarization, and inhibitors of the SK3 channel could be used for the early treatment of auricular fibrillation.

According to one embodiment, the invention relates to a compound according to the invention, as described hereinabove, for use in the treatment of a disease characterized by an insufficiency of the expression and/or activity of SK3 ion channels. Non-limiting examples of such diseases are:

- infertility. Defects in the activity or expression of SK3 may contribute to infertility. Thus, SK3 channel activators may reduce infertility by hyper-polarizing plasma membranes of smooth muscle cells;
- preterm births. A decrease in SK3 channel activity depolarizes the plasma membranes of smooth muscles, activates a potential-dependent calcium channel, the cytosolic calcium concentration increases and the uterine smooth muscles contract. On the contrary, an increase in activity of the SK3 channel hyper-polarizes the plasma membrane of myocyte and relaxes the uterine smooth muscle. Thus, SK3 channel activators could reduce uterine contractions and premature births;
- incontinence. SK3 channel activators could reduce bladder contractions and incontinence by;
- erectile dysfunctions. SK3 activators by hyper-polarizing the smooth muscle cells could relax and dilate the vascular smooth muscle of the penis; and
- systemic hypertension. The suppression of SK3 from endothelial cells reduces the EDHF pathway which leads to smooth muscle cell contraction, vasoconstriction and increased systemic blood pressure. SK3 activators by hyper-polarizing smooth muscle cells could reduce hypertension.

In one embodiment, the compound according to the invention, as described hereinabove, inhibits from more than 0% to 100% of the expression and/or activity of SK3 ion channels; preferably from 50% to 100%; even more preferably from 80% to 100% of the expression and/or activity of SK3 ion channels.

In one embodiment, the compound according to the invention, as described hereinabove, activate from more than 0% to 100% of the expression and/or activity of SK3 ion channels; preferably from 50% to 100%; even more preferably from 80% to 100% of the expression and/or activity of SK3 ion channels.

Methods for measuring the SK3 activity are well-known from the skilled artisan. A non-limiting example of such a method is disclosed in the Examples.

The present invention also concerns a pharmaceutical composition comprising at least one compound of the invention, as described hereinabove, and at least one pharmaceutically acceptable carrier for use as modulator of the expression and/or activity of SK3 ion channels.

The present invention also concerns a pharmaceutical composition comprising at least one compound of the invention, as described hereinabove, and at least one pharmaceutically acceptable carrier for use in the treatment of a disease related with a deregulation of the expression and/or activity of SK3 ion channels According to one embodiment, the pharmaceutical composition for use of the invention comprises, in addition to the at least one compound of the invention, at least one additional active ingredient, e.g., an active ingredient selected from taxanes, such as paclitaxel, docetaxel or cabazitaxel.

The compound of the invention may be used in monotherapy or in combination therapy in a subject in need of therapeutic and/or preventive treatment. Thus, according to a first embodiment, the compound of the invention is administered to the subject without any other active ingredient. Thus, according to a second embodiment, the compound of the invention is administered to the subject in combination with at least one additional active ingredient In one embodiment, the compound is administrated to the subject sequentially, simultaneously and/or separately with the other active ingredient as described hereinabove.

Preferably, the subject in need of therapeutic and/or preventive treatment is a warm-blooded animal, more preferably a human. According to one embodiment, the subject is a male. According to one embodiment, the subject is a female.

According to one embodiment, the subject is an adult, i.e. over 18 years of age. According to one embodiment, the subject is a child, i.e. under 18 years of age. According to one embodiment, the subject is an infant, i.e. having an age of more than one month and less than two years. According to one embodiment, the subject is a newborn, i.e. having an age from birth to less than one month.

This invention also relates to the use of a compound according to the invention, as described hereinabove, as a modulator of the expression and/or activity of SK3 ionic channels.

This invention also relates to the use of a compound according to the invention, as described hereinabove, in the treatment of a disease related with a deregulation of the expression and/or activity of SK3 ionic channels.

This invention also relates to the use of a compound according to the invention, as described hereinabove, in the manufacture of a medicament for the treatment of a disease related with a deregulation of the expression and/or activity of SK3 ionic channels.

This invention also relates to a method for the treatment of a disease related with a deregulation of the expression and/or activity of SK3 ionic channels in a subject in need thereof, comprising a step of administering to said subject a therapeutically effective amount of a compound according to the invention, as described hereinabove.

Methods of Administration

The compounds of the invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin. Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavouring and colouring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables. The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the present invention are employed.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, preferably between 2 and 150 mg of at least one compound of the invention, e.g. about 2, 4, 8, 16, 32, 64 or 128 mg per unit dosage.

In the treatment or prevention of conditions related with a deregulation of the expression and/or activity of SK3 ionic channels, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

EXAMPLES

The present invention is further illustrated by the following examples.

Example 1: Synthesis of Glycolipids Compounds of the Invention

Material and Methods

All materials were obtained from commercial suppliers and used without further purification. Thin-layer chromatography was performed on TLC plastic sheets of silica gel 60F254 (layer thickness 0.2 mm) from Merck. Column chromatography purification was carried out on silica gel 60 (70-230 mesh ASTM, Merck). Melting points were determined either on a digital melting point apparatus (Electrothermal IA 8103) and are uncorrected or on a Kofler bench type WME (Wagner & Munz). IR, $^{1}H$, $^{19}F$ and $^{13}C$ NMR spectra confirmed the structures of all compounds. IR spectra were recorded on a Perkin Elmer Spectrum 100 FT-IR spectrometer and NMR spectra were recorded, using $CDCl_3$, $CD_3CN$, $D_2O$ or DMSO-$d_6$ as solvent, on a Bruker AC 300, Advance DRX 400 and Advance DRX 500 spectrometers, for $^{1}H$, 75 or 100 MHz for $^{13}C$ and 282 or 377 MHz for $^{19}F$ spectra. Chemical shifts (6) were expressed in parts per million relative to the signal indirectly (i) to $CHCl_3$ (δ 7.27) for $^{1}H$ and (ii) to $CDCl_3$ (δ 77.2) for $^{13}C$ and directly (iii) to $CFCl_3$ (internal standard) (δ 0) for $^{19}F$. Chemical shifts are given in ppm and peak multiplicities are designated as follows: s, singlet; br s, broad singlet; d, doublet; dd, doublet of doublet; t, triplet; q, quadruplet; quint, quintuplet; m, multiplet. mass spectrometry was recorded on a Bruker-Autoflex MALDI TOF-TOF III, LRF200CID.

General Experimental Procedures

Synthesis of Lac(OAc)$_7$-O-2-methoxy-4-S-hexadecane (butane-S-C12) 3a

A solution of lactose trichloroacetimidate 2 previously prepared in the laboratory (850 mg, 1.08 mmol, 1.0 eq.) and the corresponding thioether 1 (300 mg, 1.03 mmol, 0.95 eq.) in dry $CH_2Cl_2$ (4 mL) is stirred with molecular sieves 4 Å during one hour under inert atmosphere. At 0° C. $BF_3 \cdot Et_2O$ in dry $CH_2Cl_2$ (2 mL) (196 μL, 1.08 mmol, 1 eq.) is added dropwise and the mixture is stirred 4 hours at 0° C. under inert atmosphere. Triethylamine is added at 0° C. and the mixture is stirred during 15 minutes. The mixture is concentrated and the compound is diluted in Ethyl Acetate (20 mL), filtered on celite and concentrated to give the crude compound 3a, purified on column on silica gel (eluant: hexane/ethyl acetate (9:1 to 8:2)) to give the pure 3a with 29% yield. Rf (hexane/acetone (6/4)): 0.8; $^1H$ NMR ($CDCl_3$, 500.253): 5.33 (d, 1H, $H_{4'}$); 5.2 (t, 1H, $H_{2'}$); 5.1 (m, 1H, $H_{3'}$); 5.0-4.85 (m, 2H, $H_1+H_{1'}$); 4.6-4.4 (m, 3H, $H_{6b}+H_2+H_{1'}$); 4.2-4.0 (m, 3H, $H_{6b}+H_{6a}+H_{5'}$); 3.7-3.4 (m, 1H, $H_{5'}+H_{6a}$); 3.7-3.55 (m, 2H, $CH_2$ sn-3); 3.5-3.4 (m, 1H, CH sn-2); 3.4 (2s, 3H, $OCH_3$ two diastereoisomers); 2.7-2.6 (m, 2H, $CH_2$ sn-1); 2.52 (t, 2H, $J_{HH}$=7 Hz, $CH_2$ α fatty chain); 2.0-2.2 (m, 21H, $CH_3$ acetyl); 1.55 (qt, 2H, $J_{HH}$=7 Hz, $CH_2$ β fatty chain); 1.35 (m, 2H, $CH_2$ fatty chain); 1.3-1.2 (m, 26H, $CH_2$ fatty chain); 0.88 (t, 3H, $J_{HH}$=7 Hz, $CH_3$ fatty chain); $^{13}C$ NMR ($CDCl_3$, 125.803): 170.4 (s, C═O); 170.2 (s, C═0); 170.1 (s, C═O); 169.8 (s, C═O); 169.7 (s, C═O); 169.1 (s, C═O); 101.1 (s, Cr); 101.0-100.9 ($C_1$ two diastereoisomers); 79.8 (CH sn-2, two diastereoisomers); 76.2 (s, $C_4$); 72.6 (s, $C_5$); 71.6 (s, $C_{5'}$); 71.0 ($CH_2$ fatty chain); 70.9 ($CH_2$Sn-1); 70.7 ($C_2$); 69.5 ($CH_2$ sn-3); 69.1 (s, $C_{2'}$); 66.6 (s, $C_{4'}$); 62.0 (s, $C_6$); 60.8 (s, $C_{6'}$); 58.0-57.7 ($OCH_3$, two diastrereoisomers); 33.2 ($CH_2$ fatty chain); 33.1 ($CH_2$ α fatty chain); 32.8 (s, $CH_2$ fatty chain); 32.7 (s, $CH_2$ fatty chain); 31.9 (s, $CH_2$ fatty chain); 32.7 (s, $CH_2$ fatty chain); 31.9 (s, $CH_2$ fatty chain); 29.8 (s, $CH_2$ fatty chain); 29.7 (s, $CH_2$ fatty chain); 29.6 (s, $CH_2$ fatty chain); 29.5 (s, $CH_2$ fatty chain); 29.4 (s, $CH_2$ fatty chain); 29.2 (s, $CH_2$ fatty chain); 28.9 (s, $CH_2$ fatty chain); 22.7 (s, $CH_2$ fatty chain); 20.8 (s, $OCH_3$); 14.1 (s, $CH_3$ fatty chain)

Synthesis of Lac(OAc)$_7$-O-2-methoxy-4-S-heneicosane (butane-S-C16) 3b

A solution of lactose trichloroacetimidate 5 previously prepared in the laboratory (442 mg, 0.57 mmol, 1.0 eq.) and the corresponding thioether 1 (200 mg, 0.58 mmol, 1.02 eq.) in dry $CH_2Cl_2$ (15 mL) is stirred with molecular sieves 4 Å during one hour under inert atmosphere. At 0° C. $BF_3 \cdot Et_2O$ (28 μL, 0.23 mmol, 0.4 eq.) is added dropwise and the mixture is stirred 24 hours at room temperature under inert atmosphere. The mixture is quenched by addition of water (10 mL). The organic layer is washed twice with aqueous saturated $NaHCO_3$ solution (2×10 mL) and an aqueous saturated NaCl solution (10 mL). The organic layer is dried upon $MgSO_4$, filtered and concentrated to give the crude compound 3b. The product is purified on chromatography on silica gel (eluant:Petroleum spirit/Ethyl acetate (8:2 to 7:3)) to give the pure 3b with 51% yield. Rf (Petroleum spirit/Ethyl acetate (7:3)): 0.28; $^1H$ NMR ($CDCl_3$, 399.972): 5.33 (d, 1H, $J_{HH}$=3.2 Hz, $H_{4'}$); 5.18 (t, 1H, $J_{HH}$=10.0 Hz, $H_3$); 5.09 (dd, 1H, $J_{HH}$=10.0 Hz, $J_{HH}$=7.9 Hz, $H_{2'}$); 4.95-4.88 (m, 2H, $H_2+H_{3'}$); 4.53-4.45 (m, 3H, $H_1+H_{6a}+H_{1'}$); 4.11-4.06 (m, 3H, $H_{6b}+H_{6'a}+H_{6'b}$); 3.98-3.85 (m, 2H, $H_{5'}+H_a$ $CH_2$ sn-3); 3.78 (t, 1H, $J_{HH}$=10.0 Hz, $H_4$); 3.67-3.54 (m, 2H, $H_5+H_b$ $CH_2$ sn-3); 3.48-3.42 (m, 1H, CH sn-2); 3.39-3.38 (2 s, 3H, $OCH_3$ two diastereoisomers); 2.63-2.59 (m, 2H, $CH_2$ sn-1); 2.49 (t, 2H, $J_{HH}$=7.4 Hz, $CH_2$ α fatty chain); 2.13 (s, 3H, $CH_3$ acetyl); 2.10 (s, 3H, $CH_3$ acetyl); 2.04 (s, 3H, $CH_3$ acetyl); 2.03 (s, 9H, $CH_3$ acetyl); 1.95 (s, 3H, $CH_3$ acetyl); 1.54 (qt, 2H, $J_{HH}$=7.6 Hz, $CH_2$ β fatty chain); 1.34-1.22 (m, 26H, $CH_2$ fatty chain); 0.86 (t, 3H, $J_{HH}$=6.8 Hz, $CH_3$ fatty chain); $^{13}C$ NMR ($CDCl_3$, 125.804): 170.4 (s, C═O); 170.2 (s, C═O); 170.1 (s, C═O); 169.8 (s, C═O); 169.7 (s, C═O); 169.1 (s, C═O); 101.1 (s, $C_{1'}$); 101.0-100.9 ($C_1$ two diastereoisomers); 79.9-79.7 (CH sn-2, two diastereoisomers); 76.2 (s, $C_4$); 72.7 (s, $C_3$); 72.6 (s, $C_5$); 71.6 (s, $C_2$); 71.0 ($C_{3'}$); 70.6 ($C_{5'}$); 69.5 ($CH_2$ sn-3); 69.0 (s, $C_{2'}$); 66.6 (s, $C_{4'}$); 62.0 (s, $C_6$); 60.8 (s, $C_{6'}$); 58.1-57.7 ($OCH_3$, two diastrereoisomers); 33.2-32.8 ($CH_2$ sn-1, two diastereoisomers); 32.6 ($CH_2$ α fatty chain); 31.9 (s, $CH_2$ fatty chain); 29.7 (s, $CH_2$ fatty chain); 29.6 (s, $CH_2$ fatty chain); 29.5 (s, $CH_2$ fatty chain); 29.4 (s, $CH_2$ fatty chain); 29.3 (s, $CH_2$ fatty chain); 28.9 (s, $CH_2$ fatty chain); 22.7 (s, $CH_2$ fatty chain); 20.9 (s, $OCH_3$); 20.8 (s, $OCH_3$); 20.7 (s, $OCH_3$); 20.5 (s, $OCH_3$); 14.1 (s, $CH_3$ fatty chain); Masse (MALDI-TOF; matrix dithranol 100 mg/mL): m/z calcd for $C_{46}H_{76}O_{19}S$ $[M+Na]^+$: 987.4594, found 987.4651.

Synthesis of Lac(OH)$_7$-O-2-methoxy-3-S-hexadecane (001)

$K_2CO_3$ (182 mg, 1.32 mmol, 6 eq.) is added to a solution of 3a (200 mg, 0.22 mmol, 1.0 eq.) in MeOH (5 mL). The mixture is stirred at room temperature during 2 hours. After filtration on resin DOWEX, the filtrate is concentrated to give the crude compound 001. The crude compound is purified by column on silica gel ($CHCl_3$/MeOH (80:20)) to give the pure compound 001 with 37% yield; $^1H$ NMR (DMSO-$d_6$, 500.252): 5.10 (brs, 2H, 2 OH); 4.8 (brs, 1H, OH); 4.66 (brs, 2H, 2 OH); 4.51 (brs, 2H, 2 OH); 4.21-4.18 (m, 2H, $H_1+H_{1'}$); 3.9-3.72 (m, 3H, $H_{6a}+CH_2$ sn-3); 3.58-3.54 (m, 3H, $H_5+H_{6b}+H_{4'}$); 3.53-3.42 (m, 5H, $H_{5'}+H_{6'a}+H_{6'b}+H_{6b}$+CH sn-2); 3.42-3.27 (m, 7H, $H_3+H_4+H_{2'}+H_{3'}$ +$OCH_3$); 2.99 (m, 1H, $H_2$); 2.70-2.57 (m, 2H, $CH_2$ sn-1); 2.60-2.50 (m, 4H, $CH_2$ α fatty chain+DMSO); 1.51-1.48 (m, 1H, $CH_2$ β fatty chain); 1.32-1.28 (m, 2H, $CH_2$ fatty chain); 1.23 (s, 24H, $CH_2$ fatty chain); 0.87-0.83 (t, 3H, $J_{HH}$=7 Hz, $CH_3$ fatty chain); $^{13}C$ NMR (DMSO-$d_6$, 125.803): 103.9 (s, C1'); 103.0-102.9 (C1 diastereoisomers); 80.8 ($C_4$) 79.6-79.5 (CH sn-2, diastereoisomers); 75.5 (s, $C_{5'}$); 75.0 (s, $C_3$); 74.9 (s, $C_5$); 73.3 (s, $C_2$); 73.1 (s, $C_{3'}$); 70.6 ($C_{2'}$); 69.5-69.3 ($CH_2$ sn-3, diastereoisomers); 68.1 ($C_{4'}$); 60.5-60.4 (2s, C6+C6'); 57.0-56.9 ($OCH_3$, diastereoisomers); 32.4-32.2 ($CH_2$ sn-1, diastereoisomers); 32.1 ($CH_2$ α fatty chain); 31.4 (s, $CH_2$ fatty chain); 29.3 (s, $CH_2$ fatty chain); 29.1 (s, $CH_2$ fatty chain); 28.8 (s, $CH_2$ fatty chain); 28.7 (s, $CH_2$ fatty chain); 28.3 (s, $CH_2$ fatty chain); 22.2 (s, $CH_2$ fatty chain); 14.0 (s, $CH_3$ fatty chain); Masse (MALDI-TOF; matrix dithranol 100 mg/mL): m/z calcd for $C_{28}H_{54}O_{12}S$ $[M+K]^+$: 653.297, found: 653.412

Synthesis of Lac(OH)7-O-2-methoxy-3-S-heneicosane (002)

$K_2CO_3$ (2.8 mL, 0.02 mmol, 0.5 eq.) is added to a solution of 3b (40 mg, 0.10 mmol, 1.0 eq.) in MeOH (5 mL). The mixture is stirred at room temperature during 15 hours. Amberlyst IR-120 ($H^+$) is added and the mixture is stirred 30 minutes at room temperature. The reaction is warmed (reflux), quickly filtered and concentrated to give the crude compound 002 with a quantitative yield; $^1$H NMR (DMSO-$d_6$, 500.133): 5.12-5.10 (m, 2H, 2 OH); 4.80 (brs, 1H, OH); 4.68-65 (m, 2H, 2 OH); 4.52-4.50 (m, 2H, 2 OH); 4.22-4.20 (m, 2H, $H_1$+$H_{1'}$); 3.83-3.72 (m, 3H, $H_{6a}$+$CH_2$ sn-3); 3.62-3.60 (m, 3H, $H_5$+$H_{6b}$+$H_{4'}$); 3.53-3.43 (m, 4H, $H_{5'}$+$H_{6'a}$+$H_{6'b}$+CH sn-2); 3.36-3.27 (m, 7H, $H_3$+$H_4$+$H_{2'}$+$H_{3'}$+$OCH_3$); 3.00-2.98 (m, 1H, $H_2$); 2.70-2.64 (m, 1H, $H_a$ $CH_2$ sn-1); 2.60-2.50 (m, 3H, $CH_2$ α fatty chain+$H_b$ $CH_2$ sn-1); 1.52-1.47 (m, 2H, β $CH_2$ fatty chain); 1.32-1.23 (m, 26H, $CH_2$ fatty chain); 0.85 (t, 3H, $J_{HH}$=6.8 Hz, $CH_3$ fatty chain); $^{13}$C NMR (DMSO-$d_6$, 125.803): 103.9 (s, $C_{1'}$); 103.0-102.9 (C1 diastereoisomers); 80.8 ($C_4$) 79.6-79.5 (CH sn-2, diastereoisomers); 75.5 (s, $C_{5'}$); 75.0 (s, $C_3$); 74.9 (s, $C_5$); 73.3 (s, $C_2$); 73.1 (s, $C_{3'}$); 70.6 ($C_{2'}$); 69.5-69.3 ($CH_2$ sn-3, diastereoisomers); 68.1 ($C_{4'}$); 60.5-60.4 (2s, $C_6$+$C_{6'}$); 57.0-56.9 ($OCH_3$, diastereoisomers); 32.4-32.2 ($CH_2$ sn-1, diastereoisomers); 32.1 ($CH_2$ α fatty chain); 31.4 (s, $CH_2$ fatty chain); 29.3 (s, $CH_2$ fatty chain); 29.1 (s, $CH_2$ fatty chain); 28.8 (s, $CH_2$ fatty chain); 28.7 (s, $CH_2$ fatty chain); 28.3 (s, $CH_2$ fatty chain); 22.2 (s, $CH_2$ fatty chain); 14.0 (s, $CH_3$ fatty chain); Masse (MALDI-TOF; matrix dithranol 100 mg/mL): m/z calcd for $C_{32}H_{62}O_{12}S$ $[M+Na]^+$: 693.3854, found 693.3804.

Synthesis of 2-methoxy-but-3-en-1-ol 4a

To a stirred solution of butadiene oxide (575 μL, 7.13 mmol, 1.0 eq.) in methanol (7 mL) is added $Al(OTf)_3$ (3.4 mg, 0.007 mmol, 0.001 eq.) in methanol (3 mL) dropwise. The mixture is stirred at 100° C. during 1 hour (oil bath temperature). The solvent is removed carefully under vacuum (T=25° C., P=160 mbar) to obtain quantitatively the compound 4a as a colorless liquid. Rf (Petroleum spirit/Ethyl acetate (1:1)): 0.65; $^1$H NMR ($CDCl_3$, 399.972): 5.65-5.57 (m, 1H, $H_3$); 5.28-5.22 (m, 2H, $CH_2H_4$); 3.67-3.63 (m, 1H, $H_2$); 4.51-3.45 (m, 2H, $CH_2H_1$); 3.28 (s, 3H, $OCH_3$); $^{13}$C NMR ($CDCl_3$, 75.5): 134.9 (CH alcene); 119.4 ($CH_2$ alcene); 83.5 (CH); 65.3 ($CH_2$); 56.6 ($OCH_3$); Masse (MALDI-TOF; matrix DCTB 10 mg/mL): m/z calcd for $C_5H_{10}O_2$[M]: 102,0675, found 102.0659.

Synthesis of 2-ethoxy-but-3-en-1-ol 4b

To a stirred solution of butadiene oxide (575 μL, 7.13 mmol, 1.0 eq.) in ethanol (7 mL) id added $Al(OTf)_3$ (3.4 mg, 0.007 mmol, 0.001 eq.) in ethanol (3 mL) dropwise. The mixture is stirred at 100° C. during 1 hour (heater block insert). The solvent is removed carefully under vacuum (T=25° C., P=6 mbar) to obtain the compound 4b as a colorless liquid with 87% yield. Rf (Petroleum spirit/Ethyl acetate (1:1)): 0.67; $^1$H NMR ($CDCl_3$, 399.920): 5.73-5.65 (m, 1H, $H_3$); 5.34-5.25 (m, 2H, $CH_2H_4$); 3.85-3.81 (m, 1H, $H_2$); 3.69-3.49 (m, 3H, $CH_2H_1$+$CH_2$OEt); 3.43-3.38 (m, 1H, $CH_2H_{1'}$); 1.22-1.19 (t, 3H, $J_{HH}$=7.2 Hz $CH_3$OEt); $^{13}$C NMR ($CDCl_3$, 75.5): 135.3 (CH alcene); 117.8 ($CH_2$ alcene); 81.4 (CH); 64.9 ($CH_2$OEt); 63.8 ($CH_2$); 14.8 ($CH_3$OEt);

Synthesis of the 4-(hexadecylthio)-2-methoxybutan-1-ol 6a

Compound 4a (200 mg, 1.96 mmol, 1.0 eq.) and 1-hexadecanethiol (1.81 mL, 5.87 mmol, 3.0 eq.) are mixed under argon. DMPA (20 mg, 10% wt) is added and the solution is placed under UV 24 hours at room temperature. The product is purified by chromatography on silica gel (eluant:petroleum spirit/ethyl acetate (8:2)) to give the pure 6a with 32% yield. Rf (Petroleum spirit/Ethyl acetate (8:2)): 0.50; $^1$H NMR ($CDCl_3$, 399.992): 3.73 (ABX, part A, dd, 1H, $J_{HH}$=11.6 Hz, $J_{HH}$=3.6 Hz, $H_a$ $CH_2H_A$)); 3.51 (ABX, part B, dd, 1H, $J_{HH}$=11.6 Hz, $J_{HH}$=5.2 Hz, $H_b$ $CH_2H_A$)); 3.40 (s, 4H, $H_B$+$OCH_3$); 2.57 (t, 2H, $J_{HH}$=7.0 Hz, $CH_2$ α fatty chain); 2.51 (t, 2H, $J_{HH}$=7.2 Hz, $CH_2H_D$); 1.88 (h, 1H, $J_{HH}$=6.8 Hz, $H_a$ $CH_2H_C$); 1.77 (h, 1H, $J_{HH}$=6.8 Hz, $H_b$ $CH_2H_C$); 1.59 (qt, 2H, $J_{HH}$=7.4 Hz, $CH_2$ β fatty chain); 1.35-1.119 (m, 26H, $CH_2$ fatty chain); 0.88 (t, 3H, $J_{HH}$=6.6 Hz, $CH_3$ fatty chain); $^{13}$C NMR ($CDCl_3$, 75.474): 80.2 ($C_B$); 63.4 ($C_A$); 57.3 ($OCH_3$); 32.2 ($CH_2$ (fatty chain); 31.9 ($CH_2$ fatty chain); 30.6 ($C_C$); 29.7; 29.5; 29.3; 29.2; 28.9; 27.9 ($C_D$+$CH_2$ fatty chain); 22.7 ($CH_2$ fatty chain); 14.1 ($CH_3$ fatty chain); masse (ESI, 100 mg/mL): m/z calcd for $C_{21}H_{44}O_2S$ [M]: 360.31, found 399.35 $[M+K]^+$.

Synthesis of the 4-(hexadecylthio)-2-ethoxybutan-1-ol 6b

Compound 4b (400 mg, 3.44 mmol, 1.0 eq.) and 1-hexadecanethiol (3.2 mL, 10.3 mmol, 3.0 eq.) are mixed under nitrogen. DMPA (20 mg, 10% wt) is added and the solution is placed under UV 24 hours at room temperature. The product is purified by chromatography on silica gel (eluant: pentane/ethyl acetate (8:2)) to give the pure 7b as a colorless liquid with 36% yield. Rf (Pentane/Ethyl acetate (8:2)): 0.41; $^1$H NMR ($CDCl_3$, 399.922): 3.67-3.62 (m, 1H, $CH_a$ sn3); 3.57-3.52 (m, 2H, $CH_2$—OEt); 3.48-3.43 (m, 2H, $CH_b$ sn3+CH sn2); 2.55 (t, 2H, $J_{HH}$=7.2 Hz, $CH_2$ α S); 2.48 (t, 2H, $J_{HH}$=7.2 Hz, $CH_2$ α S fatty chain); 2.38 (s, 1H, OH); 1.83-1.78 (m, 1H, CHa sn1); 1.73-1.69 (m, 1H, CHb sn1); 1.55-1.49 (m, 2H, $CH_2$ βS fatty chain); 1.34-1.31 (m, 2H; $CH_2$ γS fatty chain), 1.21 (s, 23H, $CH_2$ fatty chain); 1.17 (t, 3H, $CH_3$—OEt); 0.84 (t, 3H, $CH_3$ fatty chain); $^{13}$C NMR ($CDCl_3$, 75.474): 78.5 (CH sn2); 65.3 ($CH_2$—OEt); 63.97 ($CH_2$ sn3); 32.3; 32.0; 31.2; 29.8; 29.6; 29.5; 29.4; 29.0; 28.1 ($CH_2$ αS+$CH_2$ fatty chain); 22.8 ($CH_2$ sn1) 15.7 (CH3-OEt); 14.2 ($CH_3$ fatty chain); masse (Maldi TOF/TOF, Matrix HCCA): m/z calcd for $C_{22}H_{46}O_2S$ [M]: 374.32, found 397.62 $[M+Na]^+$.

Synthesis of $Lac(OAc)_7$-O-2-methoxy-4-S-heneicosane (butane-S-C16) 7a

A solution of lactose trichloroacetimidate 2 (425 mg, 0.54 mmol, 1.0 eq.) and 6a (200 mg, 0.55 mmol, 1.02 eq.) in dry $CH_2Cl_2$ (10 mL) is stirred with molecular sieves 4 Å during one hour under inert atmosphere. At 0° C. $BF_3·Et_2O$ (27 μL, 0.216 mmol, 0.4 eq.) is added dropwise and the mixture is stirred 15 hours at room temperature under inert atmosphere. The mixture is quenched by addition of water (3 mL). The organic layer is washed twice with aqueous saturated $NaHCO_3$ solution (2×3 mL) and an aqueous saturated NaCl solution (3 mL). The organic layer is dried upon $MgSO_4$, filtered and concentrated to give the crude compound 7a which is purified by chromatography on silica gel (Eluant: Petroleum spirit/Ethyl acetate (8:2 to 6:4)) to give the pure 7a with 35% yield. Rf (Petroleum spirit/Ethyl acetate (6:4)): 0.65; $^1$H NMR ($CDCl_3$, 399.992): 5.34 (d, 1H, $J_{HH}$=2.8 Hz, $H_{4T}$); 5.19 (t, 1H, $J_{HH}$=9.4 Hz, $H_3$); 5.11 (dd, 1H, $J_{HH}$=10.2 Hz, $J_{HH}$=7.8 Hz, $H_{2'}$); 4.95-4.87 (m, 2H, $H_2$+$H_{3'}$); 4.52-4.45 (m, 3H, $H_1$+$H_{6a}$+$H_{1'}$); 4.11-4.03 (m, 3H, $H_{6b}$+$H_{6'a}$+$H_{6'b}$); 3.87-3.80 (m, 2H, $H_{5'}$+$H_a$ $CH_2H_A$); 3.80 (t, 1H, $J_{HH}$=9.4 Hz, $H_4$); 3.59-3.56 (m, 1H, $H_5$); 3.53-3.39 (m, 2H, CH $H_C$+$H_b$ $CH_2H_A$); 3.36-3.35 (2 s, 3H, $OCH_3$ diastereoisomers); 2.55-2.52 (m, 2H, $CH_2H_D$); 2.48 (t, 2H, $J_{HH}$=7.4 Hz, $CH_2$ α fatty chain); 2.13 (s, 3H, $CH_3$ acetyl); 2.10 (s, 3H, $CH_3$ acetyl);

2.04 (s, 3H, $CH_3$ acetyl); 2.02 (s, 9H, 3 $CH_3$ acetyl); 1.94 (s, 3H, $CH_3$ acetyl); 1.72-1.70 (m, 2H, $CH_2H_C$); 1.56 (qt, 2H, $J_{HH}$=7.4 Hz, $CH_2$ β fatty chain); 1.34-1.19 (m, 26H, $CH_2$ fatty chain); 0.87 (t, 3H, $J_{HH}$=6.8 Hz, $CH_3$ fatty chain); $^{13}C$ NMR ($CDCl_3$, 75.474): 170.4 (s, C═O); 170.2 (s, C═O); 170.1 (s, C═O); 169.9 (s, C═O); 169.7 (s, C═O); 169.2 (s, C═O); 101.2 (s, C1); 100.8 (s, C1); 78.6-78.4 (CB); 76.4 (s, C4); 72.8 (s, C3); 72.7 (s, $C_5$); 71.7 (s, C2); 71.1 (C3'); 70.8 ($C_{5'}$); 72.2-70.3 ($C_A$); 69.2 (s, $C_{2'}$); 66.7 (s, $C_{4'}$); 62.1 (s, $C_6$); 60.9 (s, $C_{C'}$); 58.3-57.7 (m, $OCH_3$, diastereoisomers); 32.3 (m, $CH_2$ α fatty chain); 32.0 (s, $CH_2$ fatty chain); 31.6 (s, $C_C$); 29.8; 29.5; 29.4; 29.0; 27.9 ($C_D$+$CH_2$ fatty chain); 22.8 (s, $CH_2$ fatty chain); 21.0 (s, $OCH_3$); 20.9 (s, $OCH_3$); 20.7 (s, $OCH_3$); 20.6 (s, $OCH_3$); 14.2 (s, $CH_3$ fatty chain); Masse (MALDI-TOF; matrix dithranol 100 mg/mL): m/z calcd for $C_{47}H_{78}O_{19}S$ $[M+Na]^+$: 1001.4750, found 1001.4678.

Synthesis of $Lac(OAc)_7$-O-2-ethoxy-4-S-heneicosane (butane-S-C6) 7b

A solution of lactose trichloroacetimidate 2 (1.44 g, 1.84 mmol, 1.5 eq.) and 6b (460 mg, 1.23 mmol, 1.0 eq.) in dry $CH_2Cl_2$ (15 mL) is stirred with molecular sieves 4 Å during one hour under inert atmosphere. At 0° C. $BF_3·Et_2O$ (160 μL, 0.98 mmol, 0.8 eq.) is added dropwise and the mixture is stirred 15 hours at room temperature under inert atmosphere. The mixture is quenched by addition of water (5 mL). The organic layer is washed twice with aqueous saturated $NaHCO_3$ solution (2×10 mL) and an aqueous saturated NaCl solution (10 mL). The organic layer is dried upon $MgSO_4$, filtered and concentrated to give the crude compound 7b which is purified by chromatography on silica gel (Eluant:Pentane/Ethyl acetate (7/3) to give the pure 7b with 41% yield. Rf (Pentane/Ethyl acetate (7:3)): 0.4; $^1H$ NMR ($CDCl_3$, 500.133): 5.2 (d, 1H, $^3J_{HH}$=3.0, $H_{4'}$); 5.07 (t, 1H, $J_{HH}$=9.5 Hz, $H_3$); 4.97-4.94 (dd, 1H, $J_{HH}$=10.5 Hz, $J_{HH}$=8.0 Hz, $H_{2'}$); 4.85-4.82 (m, 1H, $H_{3'}$); 4.78-4.73 (q, 1H, $J_{HH}$=9.50 Hz, $J_{HH}$=18 Hz, $H_2$); 4.43-4.34 (m, 3H, $H_1$+$H_{6a}$+$H_{1'}$); 4.01-3.94 (m, 3H, $H_{6a}$+$H_{6b}$+$H_{6b}$); 3.80 (t, 1H, $J_{HH}$=7.0 Hz, $H_{5'}$); 3.68 (t, 2H, $J_{HH}$=9.0 Hz, $H_4$+$H_{A1}$); 3.50-3.30 (m, 5H, $H_5$+$H_B$+$H_{A2}$+$CH_2$—OEt diastereoisomers); 2.45-2.33 (m, 4H, $H_D$+$CH_2$ fatty chain); 2.03-1.81 (m, 25H, $CH_3$ acetyl); 1.61-1.54 (m, 2H, $CH_2H_C$); 1.42 (qt, 2H, $J_{HH}$=7.4 Hz, $CH_2$ β fatty chain); 1.23 (m, 2H, $CH_2$ γ fatty chain); 1.11 (s, 26H, $CH_2$ fatty chain); 1.0 (t, 3H, $J_{HH}$=7.0 Hz, $CH_3$—OEt); 0.74 (t, 3H, $J_{HH}$=7.0 Hz, $CH_3$ fatty chain); $^{13}C$ NMR ($CDCl_3$, 125.771): 169.94 (s, C═O); 169.92 (s, C═O); 169.8 (s, C═O); 169.6 (s, C═O); 169.4 (s, C═O); 169.2 (s, C═O); 169.0 (s, C═O); 168.7 (s, C═O); 100.7 (s, $C_{1'}$); 100.33+100.28 (s, $C_1$α+0); 76.4-76.1 ($C_B$); 75.9 (s, $C_4$); 72.6 (s, $C_3$); 72.3 (s, $C_5$); 72.1 ($C_{A1}$); 71.3 (s, $C_2$); 70.7 ($C_{3'}$); 70.4 ($C_{A2}$) 70.3 ($C_{5'}$); 68.8 (s, $C_{2'}$); 66.4 (s, $C_{4'}$); 65.6-65.0 ($OCH_2$ diastereoisomers); 61.7 (s, $C_{6'}$); 61.0 (s, $C_6$); 31.7-31.5 (m, $CH_2$ α fatty chain+$C_C$); 30.0 (s, $CH_2$ fatty chain); 29.3, 29.2, 29.0, 28.6, 27.5, 26.5 ($C_D$+$CH_2$ fatty chain); 22.3 (s, $CH_2$ fatty chain); 20.6-20.1 (m, $OCH_3$); 15.3 (s, OEt); 13.8 ($CH_3$ fatty chain). Masse (Maldi TOF/TOF, Matrix HCCA): m/z calcd for $C_{48}H_{80}O_{19}S$ [M]: 992.501, found 1031.567 $[M+K]^+$.

Synthesis of $Lac(OH)_7$—O-2-methoxy-4-S-heneicosane (butane-S-C16) (003)

NaOMe (solution 0.5 M in MeOH, 33 μL, 0.90 mg, 0.017 mmol, 0.1 eq.) is added to a solution of 7a (163 mg, 0.17 mmol, 1.0 eq.) in methanol (10 mL). The mixture is stirred at room temperature during one hour. Amberlyst IR-120 ($H^+$) is added and the mixture is stirred 30 minutes at room temperature. The reaction is warmed to reflux, quickly filtered and concentrated to give the compound 003 with 87% yield. $^1H$ NMR (DMSO-$d_6$, 300.131): 5.12-5.09 (m, 2H, 2 OH); 4.77 (brs, 1H, OH); 4.67-64 (m, 2H, 2 OH); 4.54-4.50 (m, 2H, 2 OH); 4.22-4.19 (m, 2H, $H_1$+Hr); 3.78-3.75 (m, 2H, $H_{6a}$+$H_a$ $CH_2H_A$); 3.61-3.29 (m, 15H, $H_3$+$H_4$+$H_5$+$H_{6b}$+$H_{2'}$+$H_{3'}$+$H_{4'}$+$H_{5'}$+$H_{6'a}$+$H_{6'b}$+$H_b$ $CH_2H_A$+CH $H_B$+$OCH_3$); 3.02-3.00 (m, 1H, $H_2$); 2.54-2.44 (m, 4H, $CH_2H_D$+$CH_2$ α fatty chain); 1.72-1.62 (m, 2H, $CH_2H_C$); 1.52 (qt, 2H, $J_{HH}$=6.6 Hz, $CH_2$ β fatty chain); 1.36-1.23 (m, 26H, $CH_2$ fatty chain); 0.87 (t, 3H, $J_{HH}$=6.8 Hz, $CH_3$ fatty chain); $^{13}C$ NMR (DMSO-$d_6$, 75.474): 103.9 (s, $C_{1'}$); 102.9-102.7 ($C_1$ diastereoisomers); 80.8 ($C_4$); 78.0 ($C_B$); 75.5 (s, $C_{5'}$); 75.0 (s, $C_3$); 74.9 (s, $C_5$); 73.2 (s, $C_2$); 73.1 (s, $C_{3'}$); 70.5 ($C_{2'}$); 70.2-69.8 ($C_A$, diastereoisomers); 68.1 ($C_{4'}$); 60.6-60.4 (2s, $C_6$+$C_{6'}$); 57.0-56.8 ($OCH_3$, diastereoisomers); 31.3 ($CH_2$ α fatty chain); 32.1 ($C_C$); 29.0; 28.7; 28.6; 28.2; 27.1 ($C_D$+$CH_2$ fatty chain); 22.1 (s, $CH_2$ fatty chain); 13.9 (s, $CH_3$ fatty chain). Masse (ESI, 100 mg/mL): m/z calcd for $C_{34}H_{64}O_{12}S$ [M]: 684.41, found 707.40 $[M+Na]^+$, 723.35 $[M+K]^+$.

Synthesis of $Lac(OH)_7$—O-2-ethoxy-4-S-heneicosane (butane-S-C16) (006)

Potassium Carbonate (0.021 mg, 0.15 mmol, 0.5 eq.) is added to a solution of 7b (300 mg, 0.31 mmol, 1.0 eq.) in methanol (20 mL). The mixture is stirred at room temperature during 6 hours. Amberlyst IR-120 ($H^+$) is added and the mixture is stirred 30 minutes at room temperature. The reaction is warmed to reflux, quickly filtered and concentrated to give the compound 006 with 99% yield. $^1H$ NMR (DMSO-$d_6$, 500.251): 5.2-8 (m, 2H, 2 OH); 4.8-4.3 (m, 4H, OH); 4.67-64 (m, 2H, 2 OH); 4.22-4.19 (m, 2H, $H_1$+$H_{1'}$); 3.76-3.71 (m, 2H, $H_{6a}$+$CH_2H_A$); 3.61-3.41 (m, 15H, $H_3$+$H_4$+$H_5$+$H_{6b}$+$H_{2'}$+$H_{3'}$+$H_{4'}$+$H_{5'}$+$H_{6'a}$+$H_{6'b}$+$H_b$ $CH_2H_A$+CH $H_B$+$CH_2$—OEt); 3.0-2.98 (m, 1H, $H_2$); 2.51-2.44 (m, 4H, $CH_2H_D$+$CH_2$ α fatty chain); 1.60 (m, 1H, $CH_{C1}$); 1.49 (m, 1H, $CH_{C2}$); 1.52 (m, 1H, $CH_2$ β fatty chain); 1.33-1.22 (m, 25H, $CH_2$ fatty chain); 1.1-1.06 (m, 2H, $CH_2$—OEt); 0.87 (t, 3H, $J_{HH}$=7.0 Hz, $CH_3$ fatty chain); $^{13}C$ NMR (DMSO-$d_6$, 125.804): 103.8 (s, $C_{1'}$); 102.8+102.7 ($C_1$ diastereoisomers); 80.8 ($C_4$); 76.2 ($C_B$); 75.5 (s, $C_{5'}$); 75.0 (s, $C_3$); 74.8 (s, $C_5$); 73.2 (s, $C_2$); 73.1 (s, $C_{3'}$); 70.7 ($C_{A1}$ diastereoisomers); 70.5 ($C_{2'}$); 70.3 ($C_{A2}$, diastereoisomers); 68.1 ($C_{4'}$); 64.4+64.3 (2s, $CH_2$—OEt diastereoisomers); 60.5-60.3 (2 s, $C_6$+$C_{6'}$); 31.7 ($CH_2$ α fatty chain); 32.1 ($C_C$); 40.0; 28.9; 28.8; 28.7; 28.6; 28.1; 27.1 ($C_D$+$CH_2$ fatty chain); 22.1 (s, $CH_2$ fatty chain); 15.5 (s, $CH_3$—OEt diastereoisomers); 13.9 (s, $CH_3$ fatty chain). Masse (Maldi TOF/TOF, Matrix HCCA): m/z calcd for $C_{34}H_{66}O_{12}S$ [M]: 698.427, found 737.667 $[M+K]^+$.

Synthesis of 1-(benzyloxy)hexadecan-2-ol 9a and 1-(benzyloxy)octadecan-2-ol 9b

To a stirred solution of NaH (480 mg, 20 mmol, 1.2 eq.) in dry DMF (40 mL) is added benzylalcohol (2 g, 18.5 mmol, 1.1 eq.) dropwise. The mixture is stirred 2 hours at 80° C. and a solution of the lipid epoxide (16.8 mmol, 1 eq.) in dry DMF (10 mL) is slowly added. The reaction mixture is stirred 24 hours at 80° C. The reaction mixture is concentrated. The oil is diluted in $CH_2Cl_2$ (50 mL) and the organic layer is washed with water (30 mL) and a saturated solution of NaCl (30 mL), dried over $MgSO_4$, filtrated and concentrated to give the crude compound 9. The product is purified on chromatography on silica gel (eluant:Petroleum spirit/Ethyl acetate to give the pure 9.

9a: $C_{23}H_{40}O_2$ M=348.56 g·mol$^{-1}$; Yield: 65%; Rf (Petroleum spirit/Ethyl acetate (100:5)): 0.4; $^1$H NMR ($CDCl_3$, 400.002 MHz): 7.34 (m, 5H, —$C_6H_5$); 4.56 (s, 2H, $CH_2$—$C_6H_5$); 3.81 (m, 1H, CH sn-2); 3.52 (dd, 1H, $^3J_{HH}$=9.6 $^3J_{HH}$=2.4, $CH_{2a}$ sn-1); 3.31 (dd, 1H, $^3J_{HH}$=9.6 $^3J_{HH}$=8.8, $CH_{2b}$ sn-1); 1.50 (m, 2H, $CH_2$ β fatty chain); 1.28 (m, 26H, $CH_2$ fatty chain); 0.90 (t, 3H, $^3J_{HH}$=6.6 Hz, $CH_3$ fatty chain); $^{13}$C{1H} NMR ($CDCl_3$, 75.474 MHz): 137.7 (C quat. aromatic); 127.9 (CH aromatic); 126.5 (CH aromatic); 74.5 ($CH_2$—$C_6H_5$); 72.9 ($CH_2$ sn-3); 69.9 (CH sn-2); 32.6 ($CH_2$ sn-1); 31.6 ($CH_2$ α fatty chain); 29.4 ($CH_2$ fatty chain); 29.1 ($CH_2$ fatty chain); 25.3 ($CH_2$ fatty chain); 22.4 ($CH_2$ fatty chain); 13.8 ($CH_3$ fatty chain)

9b: $C_{25}H_{44}O_2$ M=376.62 g·mol$^{-1}$; Yield: 95%; Rf (Petroleum spirit/Ethyl acetate (100:5)): 0.2; $^1$H NMR ($CDCl_3$, 400.002 MHz): 7.34 (m, 5H, —$C_6H_5$); 4.55 (s, 2H, $CH_2$—$C_6H_5$); 3.83-3.80 (m, 1H, CH sn-2); 3.51 (dd, 1H, $^3J_{HH}$=9.4 $^3J_{HH}$=3.2, $CH_{2a}$ sn-1); 3.32 (dd, 1H, $^3J_{HH}$=9.2 $^3J_{HH}$=8.0, $CH_{2b}$ sn-1); 1.50 (m, 2H, $CH_2$ β fatty chain); 1.25 (m, 26H, $CH_2$ fatty chain); 0.88 (t, 3H, $^3J_{HH}$=6.6 Hz, $CH_3$ fatty chain).

Synthesis (((2-methoxyhexadecyl)oxy)methyl)benzene 10a and (((2-methoxyoctadecyl)oxy)methyl) benzene 10b General Procedure for the Methylation To a stirred solution of NaH (140 mg, 5.9 mmol, 1.2 eq.) in dry THF (40 mL) is added 9 (4.9 mmol, 1.0 eq.) in solution in dry THF (10 mL) dropwise. The mixture is stirred 1 hour and $CH_3I$ (0.61 mL, 9.8 mmol, 2 eq.) in solution in dry THF (25 mL) is added dropwise. The reaction mixture is heated under reflux overnight. The reaction is quenched by addition of water (few mL) and the solvent is removed. The oil is dissolved in diethyl ether (50 mL). The organic layer is washed three times with an aqueous saturated NaCl solution (3×20 mL), dried over $MgSO_4$, filtered and concentrated to give the crude compound 10 which is used without purification.

10a: $C_{24}H_{42}O_2$ M=363.32 g·mol$^{-1}$; Yield: 63%; Rf (Petroleum spirit/Ethyl acetate (100:5)): 0.3; $^1$H NMR ($CDCl_3$, 300.131 MHz): 7.35 (m, 5H, —$C_6H_5$); 4.55 (s, 2H, $CH_2$—$C_6H_5$); 3.48 (d, 2H, $^3J_{HH}$=4.8, $CH_2$ sn-1); 3.47 (s, 3H, —$OCH_3$); 3.30-3.40 (m, 1H, CH sn-2); 1.50 (m, 2H, $CH_2$ β fatty chain); 1.26 (m, 26H, $CH_2$ fatty chain); 0.88 (t, 3H, $^3J_{HH}$=6.3 Hz, $CH_3$ fatty chain).

10b: $C_{26}H_{46}O_2$ M=390.35 g·mol$^{-1}$; Yield: 70%; Rf (Petroleum spirit/Ethyl acetate (100:5)): 0.3; $^1$H NMR ($CDCl_3$, 400.002 MHz): 7.26 (m, 5H, —$C_6H_5$); 4.46 (s, 2H, $CH_2$—$C_6H_5$); 3.39 (d, 2H, $^3J_{HH}$=4.8, $CH_2$ sn-1); 3.32 (s, 3H, —$OCH_3$); 3.30-3.40 (m, 1H, CH sn-2); 1.42 (m, 2H, $CH_2$ β fatty chain); 1.16 (m, 26H, $CH_2$ fatty chain); 0.79 (t, 3H, $^3J_{HH}$=6.3 Hz, $CH_3$ fatty chain).

Synthesis of 2-methoxyhexadecan-1-ol 11a and 2-methoxyoctadecan-1-ol 11b A solution of compound 10 (1 eq.) in ethyl acetate is stirred with $Pd(OH)_2$/C (20% wt, 0.6 eq)) under hydrogen pressure (20 bars), at room temperature 12 hours. The mixture is filtered on Celite and concentrated. The alcohol 11 is obtained quantitatively without purification.

11a: $C_{17}H_{36}O_2$ M=272.27 g·mol$^{-1}$; Rf (Petroleum spirit/Ethyl acetate (100:20)): 0.20; $^1$H NMR ($CDCl_3$, 400.002 MHz): 3.67 (dd, 1H, $^3J_{HH}$=11.6 $^3J_{HH}$=3.6, $CH_{2a}$ sn-1); 3.47 (dd, 1H, $^3J_{HH}$=11.6 $^3J_{HH}$=6.4, $CH_{2b}$ sn-1); 3.39 (s, 3H, —$OCH_3$); 3.26-3.24 (m, 1H, CH sn-2); 2.16 (s large, 1H, OH); 1.54 (m, 2H, $CH_2$ β fatty chain); 1.42 (m, 2H, $CH_2$ β fatty chain); 1.26 (m, 26H, $CH_2$ fatty chain); 0.87 (t, 3H, $^3J_{HH}$=6.4 Hz, $CH_3$ fatty chain).

11b: $C_{19}H_{40}O_2$ M=300.52 g·mol$^{-1}$; Rf (Petroleum spirit/Ethyl acetate (100:5)): 0.10; $^1$H NMR ($CDCl_3$, 400.002 MHz): 3.65 (dd, 1H, $^3J_{HH}$=12.4 $^3J_{HH}$=3.6, $CH_{2a}$ sn-1); 3.47 (dd, 1H, $^3J_{HH}$=12.4 $^3J_{HH}$=6.4, $CH_{2b}$ sn-1); 3.39 (s, 3H, —$OCH_3$); 3.24-3.22 (m, 1H, CH sn-2); 2.23 (s large, 1H, OH); 1.53 (m, 2H, $CH_2$ β fatty chain); 1.41 (m, 2H, $CH_2$ β fatty chain); 1.24 (m, 26H, $CH_2$ fatty chain); 0.86 (t, 3H, $^3J_{HH}$=6.4 Hz, $CH_3$ fatty chain).

Synthesis of 2-methoxyhexadecyl 2,3,6-tri-O-acetyl-4-O-(2,3,4,6-tetra-O-acetyl-α-D-galactopyranosyl)-β-D-glucopyranoside 12a and 2-methoxyoctadecyl 2,3,6-tri-O-acetyl-4-O-(2,3,4,6-tetra-O-acetyl-α-D-galactopyranosyl)-β-D-glucopyranoside 12b A solution of lactose trichloroacetimidate (1.5 g, 1.92 mmol, 1.0 eq.) and 11 (1.93 mmol, 1.02 eq.) in dry $CH_2Cl_2$ (30 mL) is stirred with molecular sieves 4 Å during one hour under inert atmosphere. At 0° C. $BF_3·Et_2O$ (0.2 mL, 0.77 mmol, 0.4 eq.) is added dropwise and the mixture is stirred 15 hours at room temperature under inert atmosphere. The mixture is quenched by addition of water (10 mL). The organic layer is washed twice with aqueous saturated $NaHCO_3$ solution (2×10 mL) and an aqueous saturated NaCl solution (10 mL). The organic layer is dried upon $MgSO_4$, filtered and concentrated to give the crude compound 12 which is purified by chromatography on silica gel.

12a: $C_{43}H_{70}O_{19}$ M=891.00 g·mol$^{-1}$; Yield: 30%; Rf ($CH_2Cl_2$/EtOH (10:1)): 0.14; $^1$H NMR ($CDCl_3$, 500.133 MHz): 5.19 (d, 1H, $^3J_{HH}$=3.0, $H_{4'}$); 5.05 (t, 1H, $^3J_{HH}$=9.5, $H_3$); 4.95-4.91 (m, 1H, $H_{2'}$); 4.86-4.83 (m, 1H, $H_2$); 4.76-4.72 (m, 1H, $H_{3'}$); 4.42-4.39 (m, 2H, $H_1$+$H_{1'}$); 4.39-4.32 (m, 1H, $H_{6a}$); 3.97-3.95 (m, 3H, $H_{6b}$+$H_{6'}$); 3.82-3.80 (m, 1H, $H_{5'}$); 3.69-3.64 (m, 2H, $H_a$ $OCH_2$+$H_4$); 3.51-3.49 (m, 1H, $H_5$); 3.37-3.29 (m, 1H, $H_b$ $OCH_2$); 3.21-3.20 (2 s, 3H, $OCH_3$ diastereoisomers); 3.16-3.11 (m, 1H, OCH); 1.99 (s, 3H, $CH_3$ acetyl); 1.96 (s, 3H, $CH_3$ acetyl); 1.91 (s, 3H, $CH_3$ acetyl); 1.90 (s, 6H, $CH_3$ acetyl); 1.88 (s, 3H, $CH_3$ acetyl); 1.80 (s, 3H, $CH_3$ acetyl); 1.45-1.35 (m, 2H, β fatty chain); 1.10 (m, 24H, $CH_2$ fatty chain); 0.74 (t, 3H, $^3J_{HH}$=5.5 Hz, $CH_3$ fatty chain); $^{13}$C{$^1$H} NMR ($CDCl_3$, 75.474 MHz): 169.7 (s, C═O); 169.5 (s, C═O); 169.3 (s, C═O); 169.1 (s, C═O); 169.0 (s, C═O); 168.9 (s, C═O); 100.3 (s, $C_{1'}$); 100.2 (s, $C_1$); 79.8-79.4 (m, OCH, diastereoisomers); 75.6 (s, $C_4$); 72.2 (s, $C_3$); 72.0 (s, $C_5$); 71.7 (s, $OCH_2$); 71.0 (s, $C_{5'}$); 70.3 ($C_2$); 70.0 ($C_{3'}$); 69.6 (s, $C_{2'}$); 66.2 (s, $C_{4'}$); 61.5 (s, $C_6$); 60.3 (s, $C_{C'}$); 57.1-56.7 (m, $OCH_3$, diastereoisomers); 31.3; 30.6; 30.5; 29.0; 28.7; 24.6; 22.4 ($CH_2$ fatty chain); 19.9 (s, $OCH_3$); 13.5 (s, $CH_3$ fatty chain); Masse: m/z calcd for $C_{45}H_{74}O_{19}$ $[M+Na]^+$: 913.98, found 913.35.

12b: $C_{45}H_{74}O_{19}$ M=919.06 g·mol$^{-1}$; Yield: 35%; Rf ($CH_2Cl_2$/EtOH (10:1)): 0.15; $^1$H NMR ($CDCl_3$, 500.133 MHz): 5.32 (d, 1H, $^3J_{HH}$=2.8, $H_{4'}$); 5.17 (t, 1H, $^3J_{HH}$=9.0, $H_3$); 5.07 (t, 1H, $^3J_{HH}$=10.0, $H_{2'}$); 4.95-4.85 (m, 2H, $H_2$+$H_{3'}$); 4.51-4.46 (m, 3H, $H_1$+$H_{6a}$+$H_{1'}$); 4.12-4.06 (m, 3H, $H_{6b}$+$H_{6'}$); 3.87-3.84 (m, 1H, $H_{5'}$); 3.79-3.75 (m, 2H, $H_a$ $OCH_2$+$H_4$); 3.60-3.58 (m, 1H, $H_5$); 3.47-3.42 (m, 1H, $H_b$ $OCH_2$); 3.34-3.32 (2 s, 3H, $OCH_3$ diastereoisomers); 3.24-3.22 (m, 1H, OCH); 2.14 (s, 3H, $CH_3$ acetyl); 2.12 (s, 3H, $CH_3$ acetyl); 2.09 (s, 3H, $CH_3$ acetyl); 2.05 (s, 6H, 3 $CH_3$ acetyl); 2.03 (s, 3H, $CH_3$ acetyl); 2.00 (s, 3H, $CH_3$ acetyl); 1.39-1.36 (m, 2H, B fatty chain); 1.22 (m, 28H, $CH_2$ fatty chain); 0.85 (t, 3H, $^3J_{HH}$=5.5 Hz, $CH_3$ fatty chain); $^{13}$C{$^1$H} NMR ($CDCl_3$, 75.474 MHz): 170.3 (s, C═O); 170.1 (s, C═O); 170.0 (s, C═O); 169.8 (s, C═O); 169.5 (s, C═O); 169.1 (s, C═O); 101.1 (s, $C_{1'}$); 100.9 (s, $C_1$); 80.0-79.7 (m, OCH, diastereoisomers); 76.2 (s, $C_4$); 72.7 (s, $C_3$); 72.6 (s, $C_5$); 72.5 (s, $OCH_2$); 71.6 (s, $C_{5'}$); 70.9 ($C_2$); 70.7 ($C_{3'}$); 69.1 (s, $C_{2'}$); 66.6 (s, $C_{4'}$); 61.9 (s, $C_6$); 60.8 (s, $C_{6'}$); 57.8-57.3 (m, $OCH_3$, diastereoisomers); 31.8; 31.2; 31.1; 30.2; 29.8; 29.7; 29.6; 29.2; 25.2; 22.6 ($CH_2$ fatty chain); 20.8 (s, $OCH_3$); 20.7 (s, $OCH_3$); 20.6 (s, $OCH_3$); 20.4 (s, $OCH_3$); 14.0 (s, $CH_3$ fatty chain); Masse: m/z calcd for $C_{45}H_{74}O_{19}$ $[M+Na]^+$: 942.04, found 941.35.

Synthesis of 2-methoxyhexadecyl 4-O-β-D-galactopyranosyl-α-D-glucopyranoside (004) and 2-methoxyoctadecyl 4-O-β-D-galactopyranosyl-α-D-glucopyranoside (005)

$K_2CO_3$ (6 eq.) is added to a solution of 12 (1.0 eq.) in methanol (10 mL). The mixture is stirred at room temperature 45 minutes. Amberlyst IR-120 ($H^+$) is added and the mixture is stirred 30 minutes at room temperature. The reaction is warmed to reflux, quickly filtered and concentrated to give the compounds 004 and 005.

004: $C_{29}H_{56}O_{12}$ M=596.75 $g\cdot mol^{-1}$; Yield: 75%; $^1H$ NMR ($CD_3OD/CDCl_3$, 400.00 MHz): 4.85-4.71 (m, 7H, OH); 3.59-2.90 (m, 20H, $H_1+H_{1'}+H_2+H_{2'}+H_3+H_{3'}+H_4+H_{4'}+H_5+H_{5'}+H_6+H_{6'}+OCH_2+OCH+OCH_3$); 1.32 (m, 2H, $CH_2$ β fatty chain); 1.02-0.90 (m, 24H, $CH_2$ fatty chain); 0.59 (t, 3H, $^3J_{HH}$=5.2, $CH_3$ fatty chain); $^{13}C\{^1H\}$ NMR ($CD_3OD/CDCl_3$, 75.474 MHz): 104.1 (s, $C_{1'}$); 103.5-103.2 ($C_1$ diastereoisomers); 80.5 ($C_4$); 79.7 ($OCH_2$); 78.2 (s, $C_{5'}$); 78.0 (s, $C_3$); 77.8 (s, $C_5$); 73.8 (s, $C_2$); 73.7 (s, $C_{3'}$); 71.5 (s, $C_{2'}$); 69.7 (s, OCH); 68.1 ($C_{4'}$); 63.6-63.4 (2 s, $C_6+C_{6'}$); 57.3-57.0 ($OCH_3$, diastereoisomers); 32.2 (s, $CH_2$ α fatty chain); 30.9; 30.1; 30.0; 29.7; 25.7; 23.3; 23.0 (s, $CH_2$ fatty chain); 14.3 (s, $CH_3$ fatty chain).

005: $C_{31}H_{60}O_{12}$ M=624.80 $g\cdot mol^{-1}$; Yield: 88%; $^1H$ NMR ($CD_3OD/CDCl_3$, 400.00 MHz): 4.25-4.05 (m, 7H, OH); 3.69-3.15 (m, 20H, $H_1+H_{1'}+H_2+H_{2'}+H_3+H_{3'}+H_4+H_{4'}+H_5+H_{5'}+H_6+H_{6'}+OCH_2+OCH+OCH_3$); 1.32 (m, 2H, $CH_2$ β fatty chain); 1.20-1.08 (m, 26H, $CH_2$ fatty chain); 0.70 (t, 3H, $^3J_{HH}$=5.2, $CH_3$ fatty chain); $^{13}C\{^1H\}$ NMR ($CD_3OD/CDCl_3$, 75.474 MHz): 103.4 (s, $C_{1'}$); 103.0-102.7 ($C_1$ diastereoisomers); 79.9 ($C_4$); 79.5 ($OCH_2$); 75.2 (s, $C_{5'}$); 74.6 (s, $C_3$); 74.4 (s, $C_5$); 73.2 (s, $C_2$); 73.0 (s, $C_{3'}$); 70.8 (s, $C_{2'}$); 70.0 (s, OCH); 68.8 ($C_{4'}$); 61.2-60.9 (2 s, $C_6+C_{6'}$); 56.6-56.3 ($OCH_3$, diastereoisomers); 32.4 (s, $CH_2$ α fatty chain); 30.5; 30.0; 29.4; 29.0; 25.1; 24.8; 22.3 (s, $CH_2$ fatty chain); 13.6 (s, $CH_3$ fatty chain)

Synthesis of 3-(hexadecylsulfinyl)-methoxypropan-1-ol 13a

To a stirred solution of corresponding thioether 1 (198 mg, 0.571 mmol, 1.0 eq.) in dry $CH_2Cl_2$ (5 mL) is added very slowly m-CPBA (77%) (128 mg, 0.571 mmol, 1.0 eq.) in dry $CH_2Cl_2$ (5 mL) at 0° C. The mixture is stirred at 0° C. and the reaction is followed by TLC ($CH_2Cl_2$/MeOH (95:5)). The mixture is quenched with a saturated aqueous solution of $NaHSO_3$ (10 mL). The aqueous layer is extracted three times with $CH_2Cl_2$ (3×20 mL) and the combined organic layers are washed with a saturated aqueous solution of $NaHCO_3$ (30 mL) and Brine (30 mL). The organic layer is dried upon $MgSO_4$, filtered and concentrated to give the compound 13a as a white solid with 93% yield; Rf ($CH_2Cl_2$/MeOH (95:5)): 0.39; 1H NMR ($CDCl_3$, 500.133): 3.80-3.70 (m, 2H, CH sn-2+$H_a$ $CH_2$ sn-3); 3.40-3.35 (m, 1H, $H_b$ $CH_2$ sn-3); 3.40-3.35 (2 s, 3H, $OCH_3$ two diastereoisomers); 2.98-2.61 (m, 4H, $CH_2$ sn-1+$CH_2$ (fatty chain); 1.68 (qt, 2H, $J_{HH}$=7.0 Hz, $CH_2$ β fatty chain); 1.38-1.17 (m, 26H, $CH_2$ fatty chain); 0.80 (t, 3H, $J_{HH}$=7.0 Hz, $CH_3$ fatty chain); 13C RMN ($CDCl_3$, 75.475): 76.1-75.8 (CH sn-2, two diastereoisomers); 62.3-62.0 ($CH_2$ sn-3, two diastereoisomers); 57.9-57.1 ($OCH_3$, two diastereoisomers); 55.7-52.6 ($CH_2$ sn-1, two diastereoisomers); 53.2 ($CH_2$ α fatty chain); 31.9 ($CH_2$ fatty chain); 29.7 ($CH_2$ fatty chain); 29.5 ($CH_2$ fatty chain); 29.3 ($CH_2$ fatty chain); 29.2 ($CH_2$ fatty chain); 28.8 ($CH_2$ fatty chain); 22.7 ($CH_2$ fatty chain); 14.1 ($CH_3$ fatty chain); masse (ESI, 100 mg/mL): m/z calcd for $C_{20}H_{42}O_3S$ [M]: 362.29, found 363.35 $[M+H]^+$, 385.35 $[M+Na]^+$, 747.55 $[2M+Na]^+$.

Synthesis of Compound 14a

A solution of $Lac(OAc)_7OCNCCl_3$ 2 (202 mg, 0.26 mmol, 1.0 eq.) and 13a (100 mg, 0.26 mmol, 1.02 eq.) in dry $CH_2C_{12}$ (5 mL) is stirred with molecular sieves 4 Å during one hour under inert atmosphere. At 0° C. $BF_3\cdot Et_2O$ (13 μL, 0.10 mmol, 0.4 eq.) is added dropwise and the mixture is stirred 17 hours at room temperature under inert atmosphere. The mixture is quenched by addition of water (3 mL). The organic layer is washed twice with aqueous saturated $NaHCO_3$ solution (2×3 mL) and an aqueous saturated NaCl solution (3 mL). The organic layer is dried upon $MgSO_4$, filtered and concentrated. The crude compound is purified on chromatography on silica gel (Eluant:Petroleum spirit/Ethyl acetate (1:1)) to give the pure compound 14a as a colorless oil with 54% yield. Rf (Petroleum spirit/Ethyl acetate (1:1)): 0.35; 0.10; 1H NMR ($CDCl_3$, 399.972): 5.34 (d, 1H, $J_{HH}$=3.2 Hz, $H_{4'}$); 5.19 (td, 1H, $J_{HH}$=9.8 Hz, $J_{HH}$=2.8 Hz, $H_3$); 5.10 (dd, 1H, $J_{HH}$=10.4 Hz, $J_{HH}$=8.0 Hz, $H_{2'}$); 4.96-4.90 (m, 2H, $H_2+H_{3'}$); 4.53-4.46 (m, 3H, $H_1+H_{6a}+H_{1'}$); 4.12-4.06 (m, 3H, $H_{6b}+H_{6'a}+H_{6'b}$); 3.98-3.61 (m, 6H, $H_4+H_5+H_{5'}+CH_2$ sn-3+CH sn-2); 3.46-3.38 (4 s, 3H, $OCH_3$ diastereoisomers); 2.98-2.61 (m, 4H, $CH_2$ sn-1+$CH_2$ α fatty chain); 2.14 (s, 3H, $CH_3$ acetyl); 2.11 (s, 3H, $CH_3$ acetyl); 2.05 (s, 3H, $CH_3$ acetyl); 2.03 (s, 3H, $CH_3$ acetyl); 2.02 (s, 6H, 2 $CH_3$ acetyl); 1.95 (s, 3H, $CH_3$ acetyl); 1.75-1.71 (m, 2H, $CH_2$ fatty chain); 1.32-1.23 (m, 26H, $CH_2$ fatty chain); 0.87 (t, 3H, $J_{HH}$=6.8 Hz, $CH_3$ fatty chain); 13C NMR ($CDCl_3$, 75.474): 170.3 (s, C═O); 170.1 (s, C═O); 170.0 (s, C═O); 169.7 (s, C═O); 169.0 (s, C═O); 101.1 (s, $C_{1'}$); 101.0-100.6 ($C_1$ diastereoisomers); 76.1 (s, $C_4$); 74.0 (m, CH sn-2); 72.8 (s, $C_3$); 72.6 (s, $C_5$); 71.6 (s, $C_2$); 71.0 ($C_{3'}$); 70.7 ($C_{5'}$); 70.3 (m, $CH_2$ sn-3); 69.1 (s, $C_{2'}$); 66.6 (s, $C_{4'}$); 61.8 (s, $C_6$); 60.8 (s, $C_{6'}$); 58.5 (m, $OCH_3$, diastrereoisomers); 55.9 (m, $CH_2$ sn-1, diastereoisomers); 52.8 (m, $CH_2$ α fatty chain); 31.9 (s, $CH_2$ fatty chain); 29.7 (s, $CH_2$ fatty chain); 29.5 (s, $CH_2$ fatty chain); 29.4 (s, $CH_2$ fatty chain); 29.2 (s, $CH_2$ fatty chain); 28.8 (s, $CH_2$ fatty chain); 22.7 (s, $CH_2$ fatty chain); 20.9 (s, $OCH_3$); 20.8 (s, $OCH_3$); 20.6 (s, $OCH_3$); 20.5 (s, $OCH_3$); 14.1 (s, $CH_3$ fatty chain); masse (ESI, 100 mg/mL): m/z calcd for $C_{46}H_{76}O_{20}S$ [M]: 980.47, found 981.35 $[M+H]^+$.

Synthesis of $Lac(OH)_7$—O-2-methoxy-3-sulfinyl-heneicosane (007)

$K_2CO_3$ (2.8 mg, 0.02 mmol, 0.5 eq.) is added to a solution of 14a (40 mg, 0.04 mmol, 1.0 eq.) in MeOH (10 mL). The mixture is stirred at room temperature overnight. Amberlyst IR-120 ($H^+$) is added and the mixture is stirred 30 minutes at room temperature. The reaction is warmed to reflux, quickly filtered and concentrated to give the compound 007 with a quantitative yield; 1H NMR (DMSO-d6, 500.133):

5.20-5.13 (m, 1H, OH); 5.07 (brs, 1H, OH); 4.76 (brs, 1H, OH); 4.66-4.62 (m, 2H, 2 OH); 4.57-4.49 (m, 2H, 2 OH); 4.25-4.18 (m, 2H, $H_1$+H1'); 3.94-3.25 (m, 17H, H3+H4+H5+H6a+H6b+H2'+H3'+H4'+H5'+H6'a+H6'b+CH sn-2+CH2 sn-3+OCH3); 3.09-3.02 (m, 1H, H2); 3.09-2.80 (m, 2H, CH2 sn-1); 2.77-2.49 (m, 2H, CH2 α fatty chain); 1.65-1.60 (m, 2H, CH2 β fatty chain); 1.39-1.32 (m, 2H, CH2 fatty chain); 1.32-1.20 (m, 26H, CH2 fatty chain); 0.86 (t, 3H, JHH=6.8 Hz, CH3 fatty chain); 13C NMR (DMSO-d6, 125.771): 103.8 (s, C1'); 103.0-102.8 (C1 diastereoisomers); 80.7-80.6 (C4 diastereoisomers); 75.5 (s, C5'); 74.9 (brs, C3+C5); 74.7-73.7 (m, CH sn-2 diastereoisomers); 73.2 (s, C2); 73.1 (s, C3'); 70.5 (C2'); 69.6-69.2 (CH2 sn-3, diastereoisomers); 68.1 (C4'); 60.5-60.4 (2 s, C6+C6'); 57.3-56.6 (m, OCH3 diastereoisomers); 54.5-51.8 (m, CH2 sn-1 diastereoisomers); 52.5-51.3 (m, CH2 α fatty chain diastereoisomers); 31.3 (s, CH2 fatty chain); 29.0 (s, CH2 fatty chain); 28.8 (s, CH2 fatty chain); 28.7 (s, CH2 fatty chain); 28.1 (s, CH2 fatty chain); 22.1 (s, CH2 fatty chain); 13.9 (s, CH3 fatty chain)); masse (ESI, 100 mg/mL): m/z calcd for C32H62O13S [M]: 686.39, found 687.35 [M+H]+, 709.35 [M+Na]+.

Synthesis of 3-(hexadecylsulfonyl)-methoxypropan-1-ol 13b

To a stirred solution of corresponding thioether 1 (200 mg, 0.577 mmol, 1.0 eq.) in dry $CH_2Cl_2$ (10 mL) is added m-CPBA (500 mg, 2.885 mmol, 5.0 eq.) dissolved in few mL of dry $CH_2Cl_2$ at 0° C. The mixture is stirred at room temperature 4 hours. The mixture is quenched with a saturated aqueous solution of $NaHSO_3$ (10 mL). The aqueous layer is extracted three times with $CH_2Cl_2$ (3×20 mL) and the combined organic layers are washed with a saturated aqueous solution of $NaHCO_3$ (20 mL) and Brine (20 mL). The organic layer is dried upon $MgSO_4$, filtered and concentrated to give the crude compound 13b. Rf ($CH_2Cl_2$/MeOH (95:5)): 0.66; NMR 1H ($CDCl_3$, 399.992): 3.85-3.82 (m, 2H, CH sn-2+$H_a$ $CH_2$ sn-3); 3.63-3.59 (m, 1H, $H_b$ $CH_2$ sn-3); 3.43 (s, 3H, $OCH_3$); 3.37 (dd, 1H, $J_{HH}$=14.8 Hz, $J_{HH}$=8.0 Hz, $H_a$ $CH_2$ sn-1); 3.10-3.00 (m, 3H, $H_b$ $CH_2$ sn-1+$CH_2$ α fatty chain); 1.82 (qt, 2H, $J_{HH}$=6.6 Hz, $CH_2$ β fatty chain); 1.41 (qt, 2H, $J_{HH}$=6.8 Hz, $CH_2$ fatty chain); 1.36-1.23 (m, 24H, $CH_2$ fatty chain); 0.87 (t, 3H, $J_{HH}$=6.6 Hz, $CH_3$ fatty chain); RMN 13C ($CDCl_3$, 75.475): 76.4 (CH sn-2); 62.0 ($CH_2$ sn-3); 57.6 ($OCH_3$); 55.0 ($CH_2$ sn-1); 54.6 ($CH_2$ α fatty chain); 32.0 ($CH_2$ fatty chain); 29.7 ($CH_2$ fatty chain); 29.6 ($CH_2$ fatty chain); 29.4 ($CH_2$ fatty chain); 29.3 ($CH_2$ fatty chain); 29.1 ($CH_2$ fatty chain); 28.5 ($CH_2$ fatty chain); 22.7 ($CH_2$ fatty chain); 21.9 ($CH_2$ fatty chain); 14.2 ($CH_3$ fatty chain); masse (ESI, 100 mg/mL): m/z calcd for $C2_0H_{42}O_4S$ [M]: 378.28, found 401.35 $[M+Na]^+$, 442.40 [M+Na+$CH_3CN$]+, 779.55 [2M+Na]+.

Synthesis of Compound 14b

A solution of $Lac(OAc)_7OCNCCl_3$ 2 5 (202 mg, 0.26 mmol, 1.0 eq.) and 13b (100 mg, 0.26 mmol, 1.02 eq.) in dry $CH_2C_{12}$ (5 mL) is stirred with molecular sieves 4 Å during one hour under inert atmosphere. At 0° C. BF3·Et2O (13 µL, 0.10 mmol, 0.4 eq.) is added dropwise and the mixture is stirred 17 hours at room temperature under inert atmosphere. The mixture is quenched by addition of water (3 mL). The organic layer is washed twice with aqueous saturated NaHCO3 solution (2×3 mL) and an aqueous saturated NaCl solution (3 mL). The organic layer is dried upon MgSO4, filtered and concentrated. The crude compound is purified on chromatography on silica gel (Eluant:Petroleum spirit/Ethyl acetate (1:1)) to give the pure compound 14b as a colorless oil with 54% yield. Rf (Petroleum spirit/Ethyl acetate (1:1)): 0.35; 1H NMR (CDCl3, 399.972): 5.34 (d, 1H, JHH=3.2 Hz, H4'); 5.19 (t, 1H, JHH=9.8 Hz, H3); 5.12 (dd, 1H, JHH=9.8 Hz, JHH=8.0 Hz, H2'); 4.96-4.87 (m, 2H, H2+H3'); 4.52-4.47 (m, 3H, H1+H6a+H1'); 4.12-4.06 (m, 3H, H6b+H6'a+H6'b); 3.93-3.87 (m, 3H, H5'+CH sn-2+Ha CH2 sn-3); 3.78 (t, 1H, JHH=9.8 Hz, H4); 3.70-3.59 (m, 2H, H5+Hb CH2 sn-3); 3.41-3.40 (2 s, 3H, OCH3 two diastereoisomers); 3.28-3.12 (m, 1H, Ha CH2 sn-1); 3.10-2.90 (m, 3H, Hb CH2 sn-1+CH2 α fatty chain); 2.16 (s, 3H, CH3 acetyl); 2.14 (s, 3H, CH3 acetyl); 2.12 (s, 3H, CH3 acetyl); 2.05 (s, 3H, CH3 acetyl); 2.03 (s, 6H, 2 CH3 acetyl); 1.95 (s, 3H, CH3 acetyl); 1.83-1.80 (m, 2H, CH2 fatty chain); 1.42-1.24 (m, 26H, CH2 fatty chain); 0.87 (t, 3H, JHH=6.6 Hz, CH3 fatty chain); 13C NMR (CDCl3, 75.474): 170.3 (s, C═O); 170.1 (s, C═O); 170.0 (s, C═O); 169.7 (s, C═O); 169.6 (s, C═O); 169.1 (s, C═O); 101.1 (s, C1'); 100.8-100.4 (C1 two diastereoisomers); 76.1 (s, C4); 75.2-74.9 (CH sn-2, two diastereoisomers); 72.8 (s, C3); 72.6 (s, C5); 71.5 (s, C2); 71.0 (C3'); 70.7 (C5'); 69.1 (s, C2'); 68.5 (CH2 sn-3); 66.6 (s, C4'); 61.8 (s, C6); 60.8 (s, C6'); 58.0-57.7 (OCH3, two diastreroisomers); 55.0 (CH2 sn-1, two diastereoisomers); 54.8 (CH2 α fatty chain); 31.9 (s, CH2 fatty chain); 29.7 (s, CH2 fatty chain); 29.1 (s, CH2 fatty chain); 28.5 (s, CH2 fatty chain); 22.7 (s, CH2 fatty chain); 21.8 (s, CH2 fatty chain); 20.8 (s, OCH3); 20.6 (s, OCH3); 20.5 (s, OCH3); 14.1 (s, CH3 fatty chain); Masse (MALDI-TOF; matrix dithranol 100 mg/mL): m/z calcd for C46H76O21S [M+Na]+: 1019.4492, found 1019.4607.

Synthesis of $Lac(OH)_7$—O-2-methoxy-3-sulfonyl-heneicosane (008)

NaOMe (solution 0.5 M in MeOH, 48 µL, 1.3 mg, 0.03 mmol, 0.3 eq.) is added to a solution of 14a (80 mg, 0.08 mmol, 1.0 eq.) in MeOH (10 mL). The mixture is stirred at room temperature during 5 hours. Amberlyst IR-120 (H+) is added and the mixture is stirred 30 minutes at room temperature. The reaction is warmed to reflux, quickly filtered and concentrated to give the compound 008 with a quantitative yield. 1H NMR (DMSO-d6, 399.972): 5.28-5.12 (m, 2H, 2 OH); 4.85 (brs, 1H, OH); 4.71-65 (m, 2H, 2 OH); 4.60-4.52 (m, 2H, 2 OH); 4.25-4.18 (m, 2H, H1+H1'); 3.89-3.74 (m, 3H, H6a+CH sn-2+Ha CH2 sn-3); 3.61-3.30 (m, 16H, H3+H4+H5+H6b+H2'+H3'+H4'+H5'+H6'a+H6'b+Hb CH2 sn-3+OCH3+CH2 sn-1); 3.08-3.02 (m, 3H, H2+CH2 α fatty chain); 1.68 (qt, 2H, JHH=7.6 Hz, CH2 β fatty chain); 1.36-1.23 (m, 26H, CH2 fatty chain); 0.85 (t, 3H, JHH=6.8 Hz, CH3 fatty chain); 13C NMR (DMSO-d6, 125.803): 103.9 (s, C1'); 103.0-102.8 (C1 two diastereoisomers); 80.7 (C4) 75.5 (CH sn-2); 75.0 (brs, C5'+C3+C5); 73.2 (s, C2); 73.1 (s, C3'); 70.6 (C2'); 68.9-68.4 CH2 sn-3, two diastereoisomers); 68.1 (C4'); 60.5-60.4 (2 s, C6+C6'); 57.1 (OCH3); 54.1 (CH2 sn-1); 53.7 (CH2 α fatty chain); 31.3 (s, CH2 fatty chain); 29.0 (s, CH2 fatty chain); 28.7 (s, CH2 fatty chain); 28.5 (s, CH2 fatty chain); 27.7 (s, CH2 fatty chain); 22.1 (s, CH2 fatty chain); 21.1 (s, CH2 fatty chain); 14.0 (s, CH3 fatty chain); masse (ESI, 100 mg/mL): m/z calcd for C32H62O14S [M]: 702.38, found 725.35 [M+Na]+, 741.30 [M+K]+.

Example 2: Capacity of the Glycolipids Compounds to Modulate the Activity of SK3 Currents

Materials and Methods

Cell Culture

HEK293T were obtained from American Type Culture Collection (ATCC) and cultured in Dulbecco's Modified Eagle's Medium, supplemented with 10% (v:v) fetal bovine serum (Lonza, France), 1 mM pyruvate sodium (Sigma-Aldrich, France), and 1% non-essential amino acid (Sigma-Aldrich, France). Cells were grown in a humidified atmosphere at 37° C. and with 95% air and 5% $CO_2$. HEK293T cells were transduced as previously described to obtain stable expression of homotetramer SK3 channels.

Electrophysiological Recordings

Experiments were performed in the whole-cell configuration of the patch-clamp technique. The patch pipettes were filled with solution contained 145 mM KCl, 1 mM MgCl2, 1 mM Mg-ATP, 0.7 mM $CaCl_2$), 1 mM EGTA and 10 mM HEPES (PCa 6). pH was adjusted to 7.2 with KOH. The bath solution contained 140 mM NaCl, 4 mM KCl, 2 mM $CaCl_2$), 1 mM MgCl2, 10 mM HEPES, 0.33 mM NaH2PO4, and 11.5 mM D-glucose. pH was adjusted to 7.4 with NaOH. Patch-clamp experiments and data analyses were conducted as previously described (Girault, A. et al. *Current Cancer Drug Target,* 2011, 11, 1111-1125). The effects of compounds on HEK293T cells expressing SK3 were measured using a ramp protocol from +100 mV to −100 mV with a holding potential of 0 mV (500 ms duration; 4 sec intervals) to inactive endogenous potassium currents. The amplitude of the apamin-sensitive current was obtained by subtraction of the amplitude of the current before and after application of 100 nmol/L apamin (a specific SKCa blocker).

In Vitro Cell Viability.

Cell viability was determined using the tetrazolium salt reduction method (MTT). Cells were seeded onto 24-well plates at a 30,000 cells and treatment with compounds were performed 24 hours after during 48 hours. Three independent experiments were performed in parallel and these were done in triplicate.

Statistics.

Statistical analyses have been performed using SigmaStat Software (version 3.0.1a, Systat Software, Inc). Unless otherwise indicated, data were expressed as mean±standard error of the mean (N, number of experiments and n, number of cells from independent experiments). For comparison between more than two means we used Kruskal-Wallis one-way analysis of variance followed by Dunn's or Dunnet's post hoc tests as appropriate. Comparisons between two means were made using Mann-Whitney. Differences were considered significant when $p<0.05$.

Results

The capacity of the compounds 001-006 (Table 2, FIGS. 1 and 2) to modulate the activity of SK3 currents was measured using the whole cell configuration of the patch-clamp technique. For these acute tests, a concentration of 10 μM for each of the compounds was used.

The results of the patch-clamp measurements are summarized in Table 2.

TABLE 2

| | SK3 current |
|---|---|
| 001 | −9.7% ± 5.2 (N = 4) |
| 002 | +177% ± 67 (N = 4) |
| 003 | +203% ± 59 (N = 5) |
| 004 | −68.8 ± 7.2% (N = 5) |
| 005 | −86.0% ± 3.9% (N = 4) |
| 006 | −91.9% ± 1.8 (N = 4) |

First, it is observed that compound 002 acts as a strong activator of SK3 channel and that this effect is associated with the length of the lipid chain. The comparison of compounds 001 and 002 indicates that the reduction of the length of the lipid chain from 16 carbon atoms to 12 carbon atoms abolished the activating effect of compounds on SK3 channel. Without willing to be linked by any theory, it is hypothesized that a short lipid chain would reduce the membrane anchor properties of the amphiphilic compounds.

When the position of the sulfur atom was changed the compound kept its activation capacity (comparison of compounds 002 and 003).

FIG. 1 shows typical SK3 currents recorded at membrane potentials varying from −90 to +90 mV for 500 ms in control condition (vehicle) and after application of compounds 002, 003 and 006. It is observed that the amplitude of outward currents strongly increased after application of compounds 002 (FIG. 1A) and 003 (FIG. 1B). SK3 currents were analyzed at 0 mV to minimize chloride currents and showed an increased close to 200% (Table 2).

Figure 2:
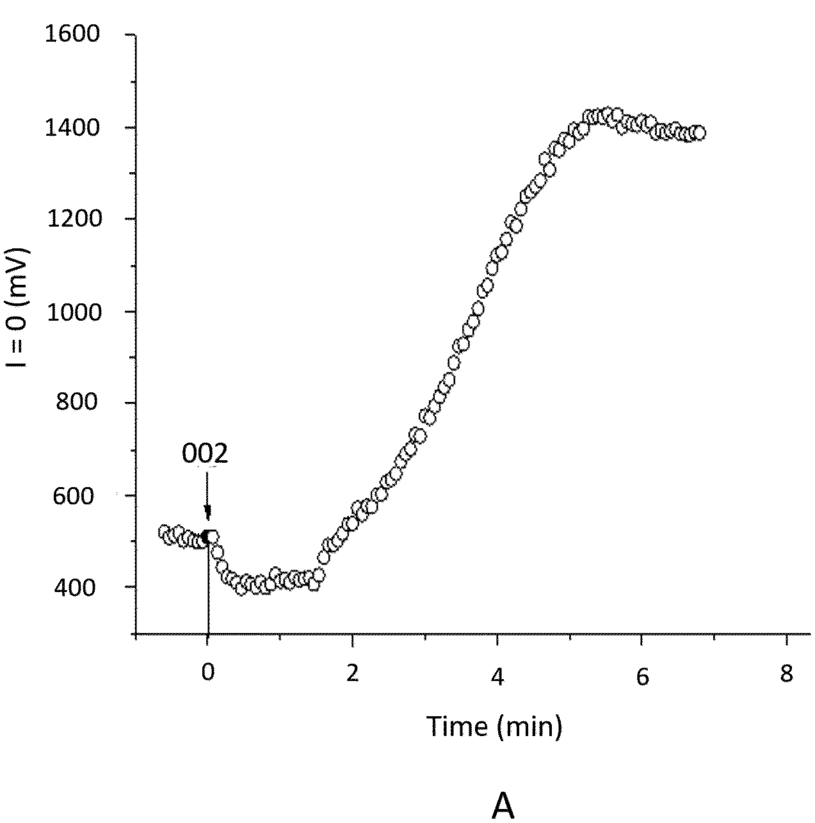
FIG. 2 (A,B,C) is a graph showing the kinetics of modulation of SK3 currents measured at 0 mV with 002 (A), 003 (B) and 006 (C). Cells were perfused with the vehicle and the moment where the vehicle is substituted by compounds of the invention is indicated by a black round.
Figure 2:
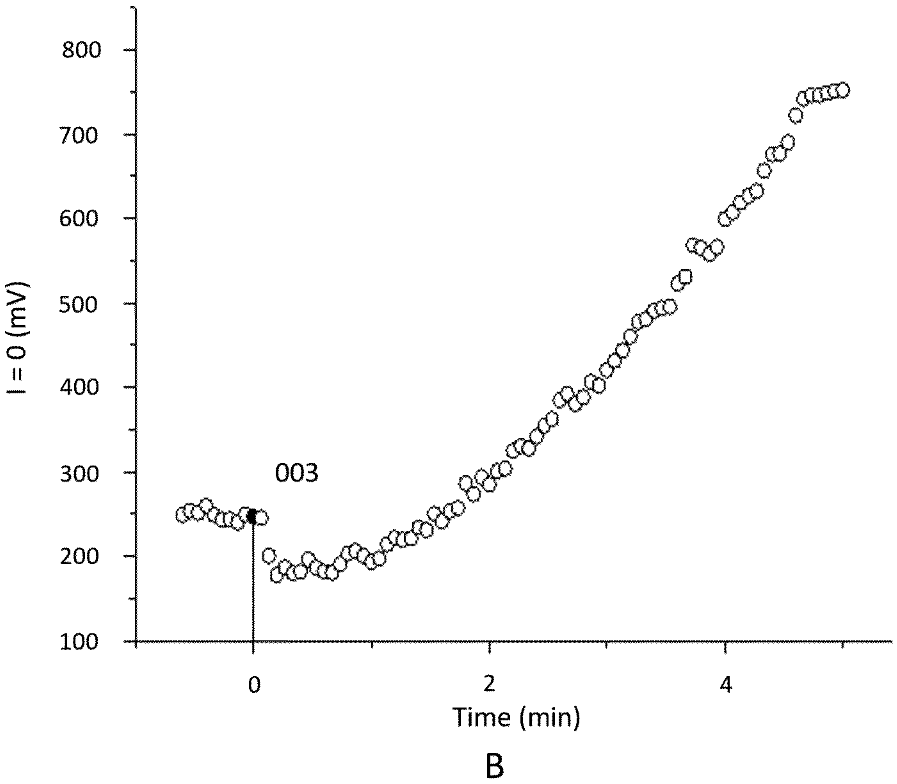

The entire time course of these experiments is depicted in FIG. 2 and it is observed a relatively slow effect of these compounds.

Indeed, it was found that the maximum of the activation was reached 5 minutes after application of either compound 002 and 003 (FIGS. 2A and 2B).

Nevertheless, these results showed for the first time that the incorporation of thioether produced the first amphiphilic activators of SK3.

It was surprisingly found by the applicant that the replacement of the sulfur in compound 002 by a $CH_2$ converted the activator 002 to a potent inhibitor of SK3 ion channel 005 that reduced SK3 currents by −86.0±3.9%

The methoxy group present in compound 003 was then replaced by an ethoxy group (compound 006).

It was surprisingly found by the applicant that such a change in the structure converted the activator 003 to an even more potent inhibitor of SK3 channel 006 that reduced SK3 currents by −91.9±1.8% (FIG. 1C). FIG. 2C shows a fast kinetic of the inhibition, with the maximum inhibitory effect reached after 30 seconds.

Figure 3:
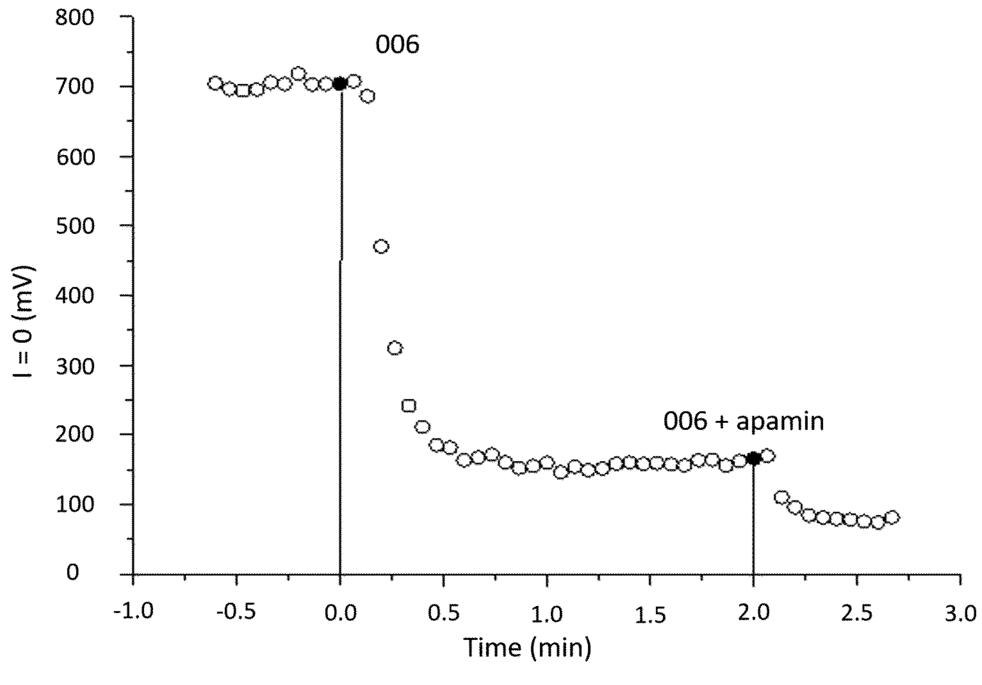
FIG. 3 is a graph showing cellular viability up to 10 μM for compounds 001-006 in MDA-MB-435s.
Figure 3:
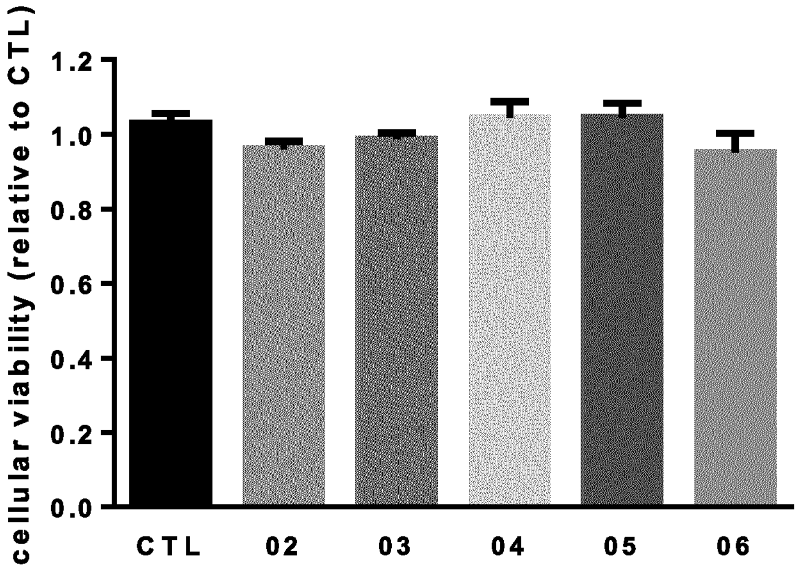

Cell viability up to 10 μM for compounds 001-006 in MDA-MB-435s (FIG. 3) and PC3 (data not shown) cells was measured after 48 hours of treatment. It was found that none of the compounds exhibited cytotoxicity up to this concentration.

CONCLUSION

The evaluation of the compounds of the invention by patch-clamp measurements indicated that compounds 001-006 of the invention are potent modulators of SK3 channels.

Especially, it was surprisingly found that the thioether-containing compound 002 exhibited a strong activation effect on SK3 (+177%±67), 30 seconds only after its addition. The presence of a shorter lipid chain (12 carbon atoms instead of 16 atoms) produce a compound with relatively more limited action on SK3.

Compound 003 featuring a thioether function shifted by one methylene unit away from the polar head group features a strong and rapid activation effect (+203%±59) on SK3 channels at 10 μM.

It was surprisingly found that the replacement of the methoxy group present in compound 003 by an ethoxy group to produce compound 006, converted the activator 003 to a potent inhibitor of SK3 channel at 10 μM (−91.9%±1.8) pointing out the great influence of the substituent present on the central oxygen atom.

Example 3: Capacity of the Glycolipids Compounds to Induce Vasodilatation by Acting on Smooth Muscle Cells

Materials and Methods

Thoracic aortic segments were isolated from a guinea pig as already indicated by Vandier et al, (Adv Physiol Educ. 2002 December; 26(1-4):195-203). Briefly, thoracic aortic segments were isolated, cleaned of adventitia, and cut into rings. The endothelium was removed and aortic rings, were mounted on stainless steel hooks and suspended in a 30-ml jacketed tissue bath with physiological salt solution (in mm): 120 NaCl, 5.4 KCl, 1 $MgCl_2$, 0.6 $NaH_2PO_4$, 25 $NaHCO_3$, 5.6 glucose, 5 Na-pyruvate, and 2 $CaCl_2$, bubbled with 95% 02-5% $CO_2$ maintained at 37° C. and aerated with 95% 02-5% $CO_2$. Solutions to be tested were directly added in the jacketed tissue bath generated allowed one to get the desired concentration around the aortic rings. Isometric force generation was recorded with Grass transducers (FT03; Quincy, MA) connected to an amplifier (gain 500) and analogic to digital converter (1 Hz) connected to a computer.

Figure 4:
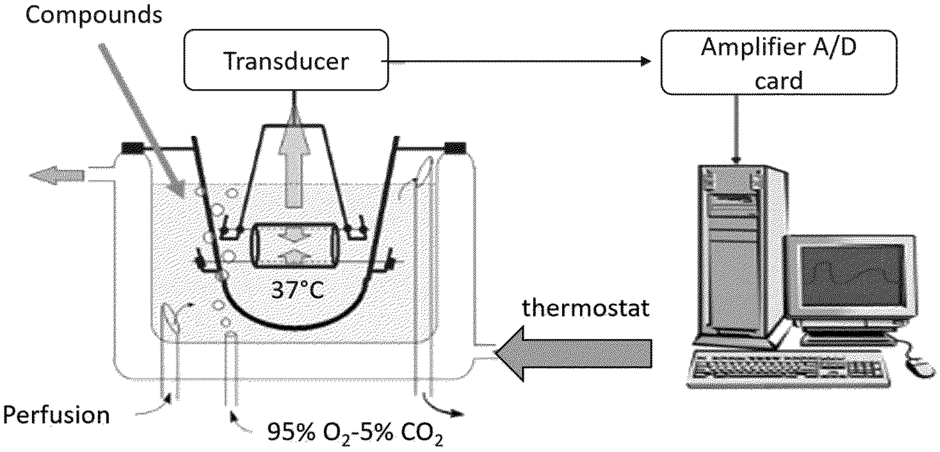
FIG. 4 is a graph showing the relaxation effect of compound 002 on pre-contracted thoracic aortic segment.
Figure 4:
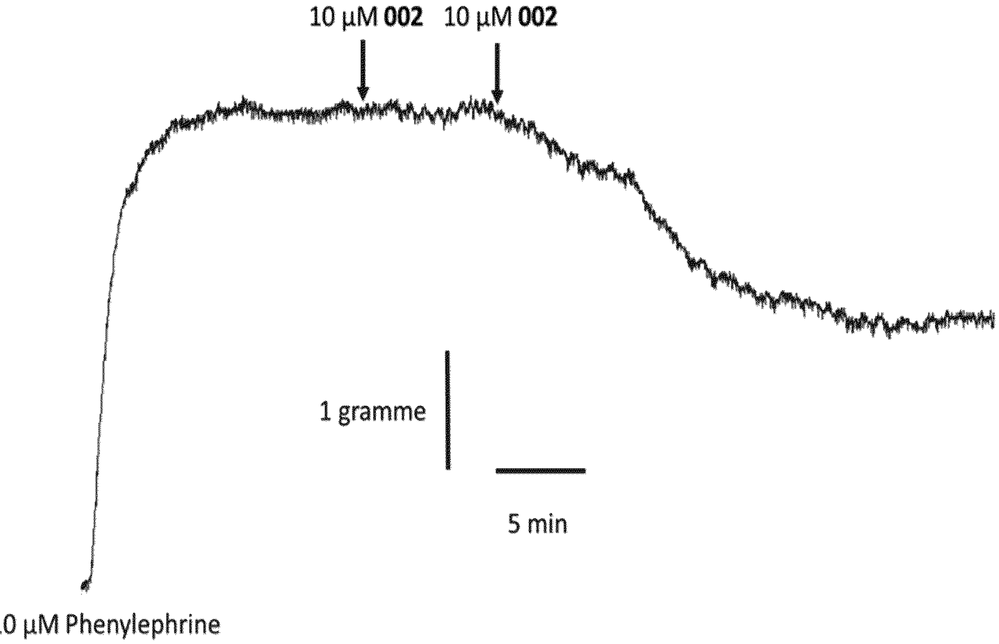

Thoracic aortic segment was pre-contracted using 10 μM phenylephrine. After the steady state was reached 10 μM of compound 002 was added, two successive times, directly in the bath solution containing a physiological salt solution, maintained at 37° C. and aerated with 95% 02-5% $CO_2$ Results FIG. 4 shows that the addition of 10 μM produces a sustained contraction. The addition, directly in the bath solution, of 10 μM compound 002 (2 times) induces a dose-dependent relaxation 5 minutes after their additions in the bath.

This result demonstrates that compound 002, by acting on smooth muscle cells (the endothelium is not functional), relaxes artery ring, suggesting that this compound may induce vasodilatation and may reduce artery pressure.

The invention claimed is:

1. A compound of Formula (II) or Formula (III):

(II)

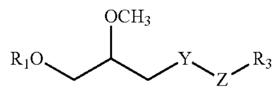

(III)

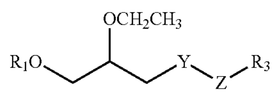

or a pharmaceutically acceptable salt or solvate thereof; wherein:

$R_1$ is a monosaccharide or a polysaccharide comprising from 2 to 6 monosaccharide units;

$R_3$ is an alkyl group comprising from 10 to 25 carbons atoms;

Y is S, and Z is $CH_2$; or Y is $CH_2$, and Z is S.

2. The compound according to claim 1, wherein $R_1$ is a polysaccharide comprising a disaccharide, the disaccharide having its monosaccharide units linked together through a α-1,4, β-1,4, α-1,6 or β-1,6 linkage.

3. The compound according to claim 2, wherein $R_1$ is a polysaccharide comprising a disaccharide, the disaccharide having its monosaccharide units linked together through a β-1,4 linkage.

4. The compound according to claim 1, wherein $R_1$ is β-D-galactopyranosyl-(1→4)-D-glucopyranose.

5. The compound according to claim 1, wherein $R_3$ is an alkyl group comprising from 15 to 18 carbon atoms.

6. The compound according to claim 1, wherein the compound is selected from:

001

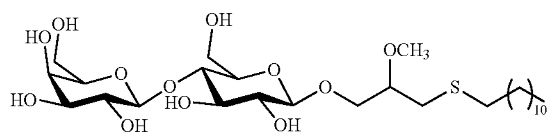

$Lac(OH)_7$-O-2-methoxy-3-S-hexadecane

002

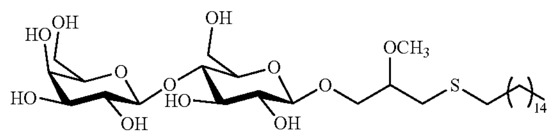

$Lac(OH)_7$-O-2-methoxy-3-S-heneicosane

003

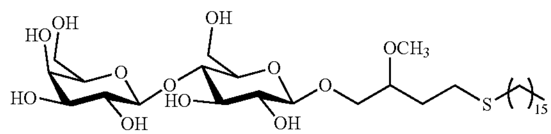

$Lac(OH)_7$-O-2-methoxy-4-S-heneicosane

006

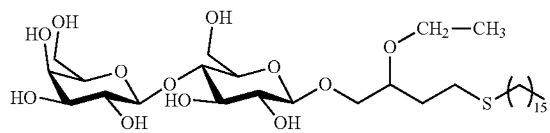

$Lac(OH)_7$-O-2-ethoxy-4-S-heneicosane or pharmaceutically acceptable salts and solvates thereof.

7. A medicament, comprising the compound according to claim 1.

8. A pharmaceutical composition, comprising the compound according to claim 1 and at least one pharmaceutically acceptable carrier.

9. A method for treating a disease characterized by an excess of the expression and/or activity of SK3 ion channels in a subject in need thereof, said disease being selected from the group consisting of cancer cell migration and metastasis, chemotherapy-induced peripheral neuropathies, central nervous system diseases, and auricular fibrillation, said method comprising administering to said subject a therapeutically effective quantity of at least one of the compound according to claim 1.

10. A method for treating a disease characterized by an insufficiency of the expression and/or activity of SK3 ion channels in a subject in need thereof, said disease being selected from the group consisting of infertility, preterm births, incontinence, erectile dysfunctions, and systemic hypertension, said method comprising administering to said subject a therapeutically effective quantity of at least one of the compound according to claim 1.

11. A method for preparing a compound according to claim 1, comprising the following steps:

(a) glycosylation of compound of formula 1:

1

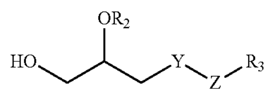

with a protected monosaccharide or polysaccharide activated at its anomeric position of formula 2:

2

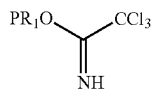

to produce compound 3:

3

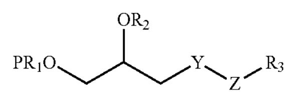

wherein Y, Z, and $R_3$ are as defined above, $R_1$ is a monosaccharide or polysaccharide comprising from 2 to 6 monosaccharide units, $R_2$ is methyl or ethyl, and P is a protecting group; and (b) deprotection of the hydroxyl groups of the compound 3 obtained in step (a) to produce the compound having the general Formula (I), (I)

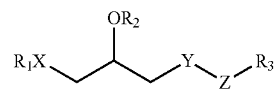

wherein Y, Z, and $R_3$ are as defined above, $R_1$ is a monosaccharide or polysaccharide comprising from 2 to 6 monosaccharide units, $R_2$ is methyl or ethyl, and X is O.

* * * * *